United States Patent [19]

Malfroy-Camine et al.

[11] Patent Number: 4,960,700
[45] Date of Patent: Oct. 2, 1990

[54] COMPOSITIONS AND METHODS FOR THE SYNTHESIS AND ASSAY OF A MAMMALIAN ENKEPHALINASE

[75] Inventors: Bernard Malfroy-Camine, San Bruno; Peter R. Schofield, San Francisco, both of Calif.

[73] Assignee: Genentech, Inc., So. San Francisco, Calif.

[21] Appl. No.: 2,478

[22] Filed: Jan. 12, 1987

Related U.S. Application Data

[63] Continuation-in-part of Ser. No. 946,566, Dec. 24, 1986.

[51] Int. Cl.$^5$ .................. C12N 9/48; C12N 9/50; C12N 5/00; C12N 1/22; C12N 15/00; C12N 1/00; C12P 21/04; C12P 19/34; C07H 15/12; C07K 13/00
[52] U.S. Cl. .................. 435/172.3; 435/212; 435/219; 435/240.2; 435/252.33; 435/71.1; 435/91; 435/172.1; 435/172.3; 435/320; 536/27; 530/350; 935/18; 935/19; 935/31; 935/41; 935/58; 935/70; 935/73; 935/82
[58] Field of Search ............... 435/68, 70, 91, 172.1, 435/172.3, 219, 212; 530/350; 935/19, 34, 70

[56] References Cited

U.S. PATENT DOCUMENTS 4,760,025 7/1988 Estell et al. .................. 435/222

OTHER PUBLICATIONS

Malfroy, B. et al, J. Biol. Chem., vol. 259, pp. 14365–14370 (1984).
Suggs et al, Proc. Natl. Acad. Sci. USA, vol. 78, pp. 6613–6617 (1981).
Milner, R. J. et al, Biochem. Soc. Symp., 1985 (publ. 1986), 52 (Mol. Neurobiol.), 107–17.
Gafford et al., Biochemistry, 22:3265–3271 (1983).
Spiess et al., J. Biol. Chem., 260(4):1979–1982 (1985).
Bos et al., Proc. Natl. Acad. Sci. USA, 81:2327–2331 (1984).
Pelade et al. (Ed.), Ann. Rev. Cell Biol., 2:292–313 (1986).
Devault et al., Embo J., 6(5):1317–1322 (1987).
Fulcher et al., Biochem. J., 240(1):305–308 (1986).
Rodriguez et al., Ed., Promoters Structure and Function, Thomas M. Roberts, pp. 452–461 (1982).

*Primary Examiner*—Robin L. Teskin
*Assistant Examiner*—Joan Ellis
*Attorney, Agent, or Firm*—Robert H. Benson; Max D. Hensley; Janet E. Hasak

[57] ABSTRACT

DNA isolates coding for enkephalinase and methods of obtaining such DNA are provided, together with expression systems for recombinant production of enkephalinase for use in therapeutic or diagnostic compositions. Enkephalinase assays are facilitated by novel enkephalinase substrates.

19 Claims, 12 Drawing Sheets

```
                                1                               10
        LysSerGluSerGlnMetAspIleThrAspIleAsnThrProLysProLysLysLysGlnArgTrpThrPro
   1    GCAAGTCAGAAAGTCAGATGGATATAACTGATATCAACACTCCAAAGCCAAAGAAGAAACAGCGATGGACTCCA 20                              30                              40
        LeuGluIleSerLeuSerValLeuValLeuLeuLeuThrIleIleAlaValThrMetIleAlaLeuTyrAlaThr
        CTGGAGATCAGCCTCTCGGTCCTTGTCCTGCTCCTCACCATCATAGCTGTGACAATGATCGCACTCTATGCAACC 50                              60
        TyrAspAspGlyIleCysLysSerSerAspCysIleLysSerAlaAlaArgLeuIleGlnAsnMetAspAlaThr
 150    TACGATGATGGTATTTGCAAGTCATCAGACTGCATAAAATCAGCTGCTCGACTGATCCAAAACATGGATGCCACC 70                              80                              90
        ThrGluProCysThrAspPhePheLysTyrAlaCysGlyGlyTrpLeuLysArgAsnValIleProGluThrSer
        ACTGAGCCTTGTACAGACTTTTTCAAATATGCTTGCGGAGGCTGGTTGAAACGTAATGTCATTCCCGAGACCAGC 100                             110
        SerArgTyrGlyAsnPheAspIleLeuArgAspGluLeuGluValValLeuLysAspValLeuGlnGluProLys
 300    TCCCGTTACGGCAACTTTGACATTTTAAGAGATGAACTAGAAGTCGTTTTGAAAGATGTCCTTCAAGAACCCAAA 120                             130                             140
        ThrGluAspIleValAlaValGlnLysAlaLysAlaLeuTyrArgSerCysIleAsnGluSerAlaIleAspSer
        ACTGAAGATATAGTAGCAGTGCAGAAAGCAAAAGCATTGTACAGGTCTTGTATAAATGAATCTGCTATTGATAGC 150                             160
        ArgGlyGlyGluProLeuLeuLysLeuLeuProAspIleTyrGlyTrpProValAlaThrGluAsnTrpGluGln
 450    AGAGGTGGAGAACCTCTACTCAAACTGTTACCAGACATATATGGGTGGCCAGTAGCAACAGAAAACTGGGAGCAA 170                             180                             190
        LysTyrGlyAlaSerTrpThrAlaGluLysAlaIleAlaGlnLeuAsnSerLysTyrGlyLysLysValLeuIle
        AAATATGGTGCTTCTTGGACAGCTGAAAAAGCTATTGCACAACTGAATTCTAAATATGGGAAAAAAGTCCTTATT 200                            210
        AsnLeuPheValGlyThrAspAspLysAsnSerValAsnHisValIleHisIleAspGlnProArgLeuGlyLeu
 600    AATTTGTTTGTTGGCACTGATGATAAGAATTCTGTGAATCATGTAATTCATATTGACCAACCTCGACTTGGCCTC 220                             230                             240
        ProSerArgAspTyrTyrGluCysThrGlyIleTyrLysGluAlaCysThrAlaTyrValAspPheMetIleSer
        CCTTCTAGAGATTACTATGAATGCACTGGAATCTATAAAGAGGCTTGTACAGCATATGTGGATTTTATGATTTCT 250                             260
        ValAlaArgLeuIleArgGlnGluGluArgLeuProIleAspGluAsnGlnLeuAlaLeuGluMetAsnLysVal
 750    GTGGCCAGATTGATTCGTCAGGAAGAAAGATTGCCCATCGATGAAAACCAGCTTGCTTTGGAAATGAATAAAGTT 270                             280                             290
        MetGluLeuGluLysGluIleAlaAsnAlaThrAlaLysProGluAspArgAsnAspProMetLeuLeuTyrAsn
        ARGGAATTGGAAAAGAAATTGCCAATGCTACGGCTAAACCTGAAGATCGAAATGATCCAATGCTTCTGTATAAC 300                             310
        LysMetThrLeuAlaGlnIleGlnAsnAsnPheSerLeuGluIleAsnGlyLysProPheSerTrpLeuAsnPhe
 900    AAGATGACATTGGCCCAGATCCAAAATAACTTTTCACTAGAGATCAATGGGAAGCCATTCAGCTGGTTGAATTTC 320                             330                             340
        ThrAsnGluIleMetSerThrValAsnIleSerIleThrAsnGluGluAspValValValTyrAlaProGluTyr
        ACAAATGAAATCATGTCAACTGTGAATATTAGTATTACAAATGAGGAAGATGTGGTTGTTTATGCTCCAGAATAT 350                             360
        LeuThrLysLeuLysProIleLeuThrLysTyrSerAlaArgAspLeuGlnAsnLeuMetSerTrpArgPheIle
1050    TTAACCAAACTTAAGCCCATTCTTACCAAATATTCTGCCAGAGATCTTCAAAATTTAATGTCCTGGAGATTCATA 370                             380                             390
        MetAspLeuValSerSerLeuSerArgThrTyrLysGluSerArgAsnAlaPheArgLysAlaLeuTyrGlyThr
        ATGGATCTTGTAAGCAGCCTCAGCCGAACCTACAAGGAGTCCAGAAATGCTTTCCGCAAGGCCCTTTATGGTACA
```

FIG.I-I

```
                      400                                    410
      ThrSerGluThrAlaThrTrpArgArgCysAlaAsnTyrValAsnGlyAsnMetGluAsnAlaValGlyArgLeu
 1200 ACCTCAGAAACAGCAACTTGGAGACGTTGTGCAAACTATGTCAATGGGAATATGGAAAATGCTGTGGGGAGGCTT 420                                    430                                    440
      TyrValGluAlaAlaPheAlaGlyGluSerLysHisValValGluAspLeuIleAlaGlnIleArgGluValPhe
      TATGTGGAAGCAGCATTTGCTGGAGAGAGTAAACATGTGGTCGAGGATTTGATTGCACAGATCCGAGAAGTTTTT 450                                    460                       Thr
      IleGlnThrLeuAspAspLeuThrTrpMetAspAlaGluThrLysLysArgAlaGluGluLysAlaLeuAlaIle
 1350 ATTCAGACTTTAGATGACCTCACTTGGATGGATGCCGAGACAAAAAAGAGAGCTGAAGAAAAGGCCTTAGCAATT
                                                                                A
              470                                    480                                    490
      LysGluArgIleGlyTyrProAspAspIleValSerAsnAspAsnLysLeuAsnAsnGluTyrLeuGluLeuAsn
      AAAGAAAGGATCGGCTATCCTGATGACATTGTTTCAAATGATAACAAACTGAATAATGAGTACCTCGAGTTGAAC 500                                    510
      TyrLysGluAspGluTyrPheGluAsnIleIleGlnAsnLeuLysPheSerGlnSerLysGlnLeuLysLysLeu
 1500 TACAAAGAAGATGAATACTTCGAGAACATAATTCAAAATTTGAAATTCAGCCAAAGTAAACAACTGAAGAAGCTC 520                                    530                                    540
      ArgGluLysValAspLysAspGluTrpIleSerGlyAlaAlaValValAsnAlaPheTyrSerSerGlyArgAsn
      CGAGAAAAGGTGGACAAAGATGAGTGGATAAGTGGAGCAGCTGTAGTCAATGCATTTTACTCTTCAGGAAGAAAT 550                                    560
      GlnIleValPheProAlaGlyIleLeuGlnProProPhePheSerAlaGlnGlnSerAsnSerLeuAsnTyrGly
 1650 CAGATAGTCTTCCCAGCCGGCATTCTGCAGCCCCCCTTCTTTAGTGCCCAGCAGTCCAACTCATTGAACTATGGG 570                                    580                                    590
      GlyIleGlyMetValIleGlyHisGluIleThrHisGlyPheAspAspAsnGlyArgAsnPheAsnLysAspGly
      GGCATCGGCATGGTCATAGGACACGAAATCACCCATGGCTTCGATGACAATGGCAGAAACTTTAACAAAGATGGA 600                                    610
      AspLeuValAspTrpTrpThrGlnGlnSerAlaSerAsnPheLysGluGlnSerGlnCysMetValTyrGlnTyr
 1800 GACCTCGTTGACTGGTGGACTCAACAGTCTGCAAGTAACTTTAAGGAGCAATCCCAGTGCATGGTGTATCAGTAT 620                                    630                                    640
      GlyAsnPheSerTrpAspLeuAlaGlyGlyGlnHisLeuAsnGlyIleAsnThrLeuGlyGluAsnIleAlaAsp
      GGAAACTTTTCCTGGGACCTGGCAGGTGGACAGCACCTTAATGGAATTAATACACTGGGAGAAAACATTGCTGAT 650                                    660
      AsnGlyGlyLeuGlyGlnAlaTyrArgAlaTyrGlnAsnTyrIleLysLysAsnGlyGluGluLysLeuLeuPro
 1950 AATGGAGGTCTTGGTCAAGCATACAGAGCCTATCAGAATTATATTAAAAAGAATGGCGAAGAAAAATTACTTCCT 670                                    680                                    690
      GlyLeuAspLeuAsnHisLysGlnLeuPhePheLeuAsnPheAlaGlnValTrpCysGlyThrTyrArgProGlu
      GGACTTGACCTAAATCACAAACAACTATTTTTCTTGAACTTTGCACAGGTGTGGTGTGGAACCTATAGGCCAGAG 700                                    710
      TyrAlaValAsnSerIleLysThrAspValHisSerProGlyAsnPheArgIleIleGlyThrLeuGlnAsnSer
 2100 TATGCGGTTAACTCCATTAAAACAGATGTGCACAGTCCAGGCAATTTCAGGATTATTGGGACTTTGCAGAACTCT 720                                    730                                    740
      AlaGluPheSerGluAlaPheHisCysArgLysAsnSerTyrMetAsnProGluLysLysCysArgValTrpOP*
      GCAGAGTTTTCAGAAGCCTTTCACTGCCGCAAGAATTCATACATGAATCCAGAAAAGAAGTGCCGGGTTTGGTGA

2250 TCTTCAAAAGAAGCATTGCAGCCCTTGGCTAGACTTGCCAACACCACAGAAATGGGGAATTCTCTAATCGAAAGA
      AAATGGGCCCTAGGGGTCACTGTACTGACTTGAGGGTGATTAACAGAGAGGGCACCATCACAATACAGATAACAT

2400 TAGGTTGTCCTAGAAAGGGTGTGGAGGGAGGAAGGGGGTCTAAGGTCTATCAAGTCAATCATTTCTCACTGTGTA
      CATAATGCTTAATTTCTAAAGATAATATTACTGTTTATTTCTGTTTCTCATATGGTCTACCAGTTTGCTGATGTC

2550 CCTAGAAAACAATGCAAAACCTTTGAGGTAGACCAGGATTTCTAATCAAAGGGAAAAGAAGATGTTGAAGAATA
      CAGTTAGGCACCAGAAGAACAGTAGGTGACACTATAGTTTAAAACACATTGCCTAACTACTAGTTTTTACTTTTA
```

FIG.1-2

```
2700 TTTGCAACATTTACAGTCCTTCAAAATCCTTCCAAAGAATTCTTATACACATTGGGGCCTTGGAGCTTACATAGT
     TTTAAACTCATTTTTGCCATACATCAGTTATTCATTCTGTGATCATTTATTTTAAGCACTCTTAAAGCAAAAAAT

2850 GAATGTCTAAAATTGTTTTTTGTTGTACCTGCTTTGACTGATGCTGAGATTCTTCAGGCTTCCTGCAATTTTCTA
     AGCAATTTCTTGCTCTATCTCTCAAAACTTGGTATTTTTCAGAGATTTATATAAATGTAAAAATAATAATTTTTA

3000 TATTTAATTATTAACTACATTTATGAGTAACTATTATTATAGGTAATCAATGAATATTGAAGTTTCAGCTTAAAA
     TAAACAGTTGTGAACCAAGATCTATAAAGCGATATACAGATGAAAATTTGAGACTATTTAAACTTATAAATCATA

3150 TTGATGAAAAGATTTAAGCACAAACTTTAGGG
```

FIG.I-3

```
  1 GCGGAGATGTGCAAGTGGCGAAGCTGGACCGAGTGCAGGCGCAAGCTGCTGAGCGGCTGAGGCGAGGGATTTTAG
                               1                              10
      MetGlyArgSerGluSerGlnMetAspIleThrAspIleAsnAlaProLysProLysLysLysGlnArgTrp
    GTGATGGCAAGATCAGAAAGTCAGATGGATATTACTGATATCAATGCTCCAAAGCCGAAGAAGAAACAGCGATGG 20                              30                              40
      ThrProLeuGluIleSerLeuSerValLeuValLeuLeuThrIleIleAlaValThrMetIleAlaLeuTyr
151 ACTCCACTGGAGATCAGCCTTTCTGTGCTCGTCTTGCTCCTGACTATCATAGCTGTGACAATGATTGCTCTCTAT 50                              60
      AlaThrTyrAspAspGlyIleCysLysSerSerAspCysIleLysSerAlaAlaArgLeuIleGlnAsnMetAsp
    GCAACCTATGATGATGGTATTTGCAAATCATCAGACTGCATAAAATCAGCTGCTCGACTGATCCAGAACATGGAT 70                              80                              90
      AlaSerAlaGluProCysThrAspPhePheLysTyrAlaCysGlyGlyTrpLeuLysArgAsnValIleProGlu
301 GCCTCTGCTGAGCCATGTACGGACTTCTTCAAATATGCTTGTGGAGGCTGGTTGAAACGCAATGTCATCCCTGAG 100                             110
      ThrSerSerArgTyrSerAsnPheAspIleLeuArgAspGluLeuGluValIleLeuLysAspValLeuGlnGlu
    ACCAGTTCCCGATACAGTAATTTTGACATTCTAAGAGATGAACTAGAAGTCATTTTGAAAGATGTCCTTCAAGAA 120                             130                             140
      ProLysThrGluAspIleValAlaValGlnLysAlaLysThrLeuTyrArgSerCysIleAsnGluSerAlaIle
451 CCCAAAACTGAGGACATAGTAGCAGTGCAGAAAGCAAAAACTTTGTACAGATCATGTATAAATGAATCTGCTATT 150                             160
      AspSerArgGlyGlyGlnProLeuLeuThrLeuLeuProAspIleTyrGlyTrpProValAlaSerGlnAsnTrp
    GATAGCAGAGGTGGGCAACCTCTGCTCACACTGTTACCAGATATATATGGGTGGCCAGTAGCATCACAAAACTGG 170                             180                             190
      GluGlnThrTyrGlyThrSerTrpThrAlaGluLysSerIleAlaGlnLeuAsnSerLysTyrGlyLysLysVal
601 GAACAAACATATGGTACTTCTTGGACAGCTGAGAAATCTATTGCACAACTGAATTCTAAATATGGGAAAAAGGTC 200                             210
      LeuIleAsnPhePheValGlyThrAspAspLysAsnSerThrGlnHisIleIleHisPheAspGlnProArgLeu
    CTCATTAATTTTTTTGTTGGCACTGATGATAAGAATTCTACCCAGCATATAATTCATTTTGACCAGCCTCGACTT 220                             230                             240
      GlyLeuProSerArgAspTyrTyrGluCysThrGlyIleTyrLysGluAlaCysThrAlaTyrValAspPheMet
751 GGCCTCCCTTCCAGAGACTACTATGAGTGTACAGGAATATATAAAGAGGCTTGCACAGCATATGTGGATTTTATG 250                             260
      IleSerValAlaArgLeuIleArgGlnGluGlnArgLeuProIleAspGluAsnGlnLeuSerLeuGluMetAsn
    ATTTCTGTGGCCAGACTGATTCGTCAGGAACAAAGATTGCCTATTGATGAAAACCAGCTCTCTTTGGAAATGAAT 270                             280                             290
      LysValMetGluLeuGluLysGluIleAlaAsnAlaThrThrLysProGluAspArgAsnAspProMetLeuLeu
901 AAAGTTATGGAATTGGAAAAAGAAATTGCCAATGCCACAACTAAACCAGAAGACCGAAATGACCCAATGCTGCTT 300                             310
      TyrAsnLysMetThrLeuAlaLysLeuGlnAsnAsnPheSerLeuGluIleAsnGlyLysProPheSerTrpSer
    TATAACAAAATGACATTGGCCAAGCTCCAAAATAACTTCTCTCTGGAGATCAATGGGAAGCCATTCAGCTGGTCA 320                             330                             340
      AsnPheThrAsnGluIleMetSerThrValAsnIleAsnIleGlnAsnGluGluGluValValValTyrAlaPro
1051 AATTTCACAAATGAAATCATGTCAACTGTGAATATTAATATTCAAAATGAGGAAGAAGTGGTTGTTTATGCTCCA 350                             360
      GluTyrLeuThrLysLeuLysProIleLeuThrLysTyrSerProArgAspLeuGlnAsnLeuMetSerTrpArg
    GAATATTTAACCAAACTTAAGCCTATTCTTACCAAATATTCTCCCAGAGATCTTCAAAATTTAATGTCCTGGAGG
```

FIG.2a-1

```
                   370                              380                              390
     PheIleMetAspLeuValSerSerLeuSerArgAsnTyrLysGluSerArgAsnAlaPheArgLysAlaLeuTyr
1201 TTCATAATGGATCTTGTAAGCAGCCTCAGCCGAAACTACAAGGAGTCCAGAAATGCTTTCCGCAAGGCCCTTTAC 400                              410
     GlyThrThrSerGluThrAlaThrTrpArgArgCysAlaAsnTyrValAsnGlyAsnMetGluAsnAlaValGly
     GGGACTACATCCGAAACTGCAACCTGGAGACGGTGTGCCAACTACGTCAATGGGAACATGGAGAATGCTGTGGGG 420                              430                              440
     ArgLeuTyrValGluAlaAlaPheAlaGlyGluSerLysHisValValGluAspLeuIleAlaGlnIleArgGlu
1351 AGGCTTTATGTGGAAGCAGCTTTTGCTGGAGAGAGCAAGCACGTGGTTGAAGATTTGATTGCACAAATCCGTGAA 450                              460
     ValPheIleGlnThrLeuAspAspLeuThrTrpMetAspAlaGluThrLysLysLysAlaGluGluLysAlaLeu
     GTTTTTATTCAGACTTTAGATGACCTCACTTGGATGGATGCTGAGACAAAAAAGAAAGCTGAAGAGAAGGCCCTG 470                              480                              490
     AlaIleLysGluArgIleGlyTyrProAspAspIleIleSerAsnGluAsnLysLeuAsnAsnGluTyrLeuGlu
1501 GCAATTAAAGAAAGGATTGGCTATCCTGATGACATCATCTCCAATGAGAATAAACTGAATAATGAGTATCTTGAG 500                              510
     LeuAsnTyrLysGluGluGluTyrPheGluAsnIleIleGlnAsnLeuLysPheSerGlnSerLysGlnLeuLys
     TTGAACTACAAGGAAGAGGAATACTTTGAGAACATAATTCAAAATTTGAAATTCAGCCAAAGCAAGCAGCTAAAG 520                              530                              540
     LysLeuArgGluLysValAspLysAspGluTrpIleSerGlyAlaAlaValValAsnAlaPheTyrSerSerGly
1651 AAGCTCCGAGAAAAGGTGGACAAAGATGAGTGGATAAGTGGCGCGGCGGTAGTCAATGCATTTTATTCCTCAGGC 550                              560
     ArgAsnGlnIleValPheProAlaGlyIleLeuGlnProProPhePheSerAlaArgGlnSerAsnSerLeuAsn
     AGAAATCAGATCGTCTTCCCCGCCGGCATTTTGCAGCCCCCATTCTTTAGTGCTCGGCAGTCCAACTCATTGAAC 570                              580                              590
     TyrGlyGlyIleGlyMetValIleGlyHisGluIleThrHisGlyPheAspAspAsnGlyArgAsnPheAsnLys
1801 TATGGGGGCATCGGCATGGTCATCGGACATGAAATCACACATGGCTTTGATGACAATGGCAGAAATTTTAACAAA 600                              610
     AspGlyAspLeuValAspTrpTrpThrGlnGlnSerAlaAsnAsnPheLysAspGlnSerGlnCysMetValTyr
     GATGGAGACCTCGTTGACTGGTGGACTCAGCAGTCTGCAAATAATTTCAAAGACCAATCCCAGTGTATGGTGTAC
                                                                 C
                   620                              630                              640
     GlnTyrGlyAsnPheThrTrpAspLeuAlaGlyGlyGlnHisLeuAsnGlyIleAsnThrLeuGlyGluAsnIle
1951 CAGTATGGAAACTTTACATGGGACCTAGCAGGTGGACAGCATCTCAATGGAATTAACACACTAGGAGAAAATATT 650                              660
     AlaAspAsnGlyGlyIleGlyGlnAlaTyrArgAlaTyrGlnAsnTyrValLysLysAsnGlyGluGluLysLeu
     GCTGATAATGGAGGGATTGGCCAAGCATACAGAGCCTATCAGAATTATGTTAAAAAGAATGGTGAAGAAAAATTA 670                              680                              690
     LeuProGlyLeuAspLeuAsnHisLysGlnLeuPhePheLeuAsnPheAlaGlnValTrpCysGlyThrTyrArg
2101 CTCCCTGGACTTGACCTCAATCACAAACAACTATTCTTCTTGAACTTTGCCCAGGTGTGGTGTGGAACCTACCGG 700                              710
     ProGluTyrAlaValAsnSerIleLysThrAspValHisSerProGlyAsnPheArgIleIleGlyThrLeuGln
     CCAGAGTATGCAGTCAATTCCATTAAAACAGATGTACACAGTCCTGGCAATTTCAGGATCATTGGGACTTTGCAG 720                              730                              740
     AsnSerAlaGluPheAlaAspAlaPheHisCysArgLysAsnSerTyrMetAsnProGluArgLysCysArgVal
2251 AACTCTGCTGAGTTTGCGGATGCCTTTCATTGCCGCAAGAACTCATACATGAATCCAGAAAGGAAATGTCGGGTT

TrpOP*
     TGGTGATCTTCACAGGAAGTGGAGCATCCATGGCAGGACTCGCCAAAGCCACAGAAACAGGAAGTCTTCCCTCAG
```

FIG.2a-2

2401 AGAACGTGGGCCCCGGAAGTTTCTTCAGCTTCTTGGGGGAAATTCACAGAGATGAGCACGAGCTAACAAAAATGA
AATTAGATTATTAAAACCGCTGTGAATGAAAGGGGAGAAAACCTACGATCTAGCAAATCAATCACTTCACTGTGT

2551 AAATAATTACCTTCCAACGGTAATATTACCGTTCACTTCTGGTTCTCACACAGACTGCAGCTTTCATGCTGTCTG
TAGAGAACAGTGTTAACACTTAAAGCAGGTTATGACTTCTGATCAAGAGGAGGAAGACGCTGAATACAGTTGGGC

2701 ACCAAAGTACAGATTTGCCTCTCAGCACTCACTTTTGTTTGCAACATTCAGCTCCTTCAAAATTCTCCCAAAGAA
CCCCCATGCATACTGTGGCCTTCAGGCTCCTGCAGTGTGGAACTCATTTTACCATGCATAAATTATTCATTCATT

2851 CCACATCATTTTAGTTTGAGCACTCTTAGAGCTTAAACTAGAGAGTCTGAAATGGTTCCGCCATTTACCCACTTG
AGTGGTGTTGAGACTCTTCAGCCCCCTACAGATTTTGAGCAATTTCTTGCTCTCGCTGCCCCTCAGACTTAGTC
A

3001 TTTTAAAGGATTTGTAGTAATGTATAAAAAACATTCTATATTTAATTATTAACTACACATGACCAAATAAACCAT
TGCTATAGGTAATCATTGAATATTGACATTATATGGCCAAGATAGATAGTTAAGAAGATCTGTAACATGATGTGC

3151 AGATGAAAATTTGAAACTTTTTAAGCCTGTAAATCATATTGCTGAAAATCTTCAAACACAAACTCTGGGGTGAGC
ATTACCATTGAACAGTTG

FIG.2a-3

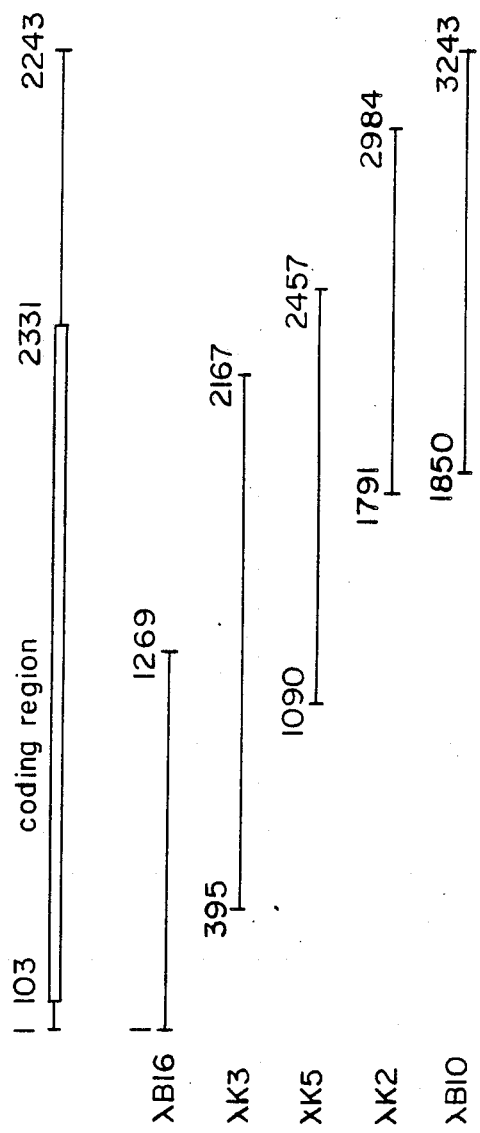

COMPOSITIONS AND METHODS FOR THE SYNTHESIS AND ASSAY OF A MAMMALIAN ENKEPHALINASE

This is a continuation-in-part of U.S. Ser. No. 06/946,566, now abandoned filed Dec. 24, 1986.

BACKGROUND OF THE INVENTION

This invention relates to enkephalinase, also known as neutral endopeptidase or kidney brush border neutral proteinase (E.C. 3.4.24.11, recommended name of the Enzyme Commission). The invention further relates to novel forms and compositions thereof and particularly to the means and methods for production of enkephalinase to homogeneity in therapeutically significant quantities. This invention also relates to preparation of isolated deoxyribonucleic acid (DNA) coding for the production of enkephalinase; to methods of obtaining DNA molecules which code for enkephalinase; to the expression of human and mammalian enkephalinase utilizing such DNA, as well as to novel compounds, including novel nucleic acids encoding enkephalinase or fragments thereof. This invention is also directed to enkephalinase derivatives, particularly derivatives lacking cytoplasmic and/or transmembrane portions of the protein, and their production by recombinant DNA techniques.

Enkephalinase has been purified from kidney (Kerr, M. A. and Kenny, A. J. Biochem. J. 137: 477-488 [1974], Gafford, J. et al., Biochemistry 22, 3265-3271 [1983] and Malfroy, B. and Schwartz, J. C., *Life Sci.* 31, 1745-1748 [1982]), intestine (Danielsen, E. M. et al., Biochem. J. 191, 545-548 [1980]), pituitary (Orlowski, M. and Wilk, S. Biochemistry 20: 4942-4945 [1981]), brain (Relton, J. M. et al., Biochem. J. 215: 755-762 [1983]) and lymph nodes (Bowes, M. A. and Kenny, A. J., Biochem. J. 236: 801-810 [1986]), and has been detected in many peripheral organs (Llorens, C. and Schwartz, J. C., Eur. J. Pharmacol. 69, 113-116 (1981) and in human neutrophils (Connelly, J. C. et al., Proc. Natl. Acad. Sci.[U.S.A.] 82: 8737-8741 [1985]). The distribution of enkephalinase in the brain closely parallels that of the enkephalins. Llorens, C. et al., J. Neurochem. 39: 1081-1089 (1982). Enkephalinase is also present in those peripheral tissues and cells that respond to and/or release various endogenous peptides. Enkephalinase is a membrane-bound glycoprotein with subunit $M_r$ values in the range of 87000 to 94000. Variation in the $M_r$ values are attributed to differences in the extent and pattern of glycosylation.

The substrate specificity of enkephalinase has been studied using the enzyme from rat and human kidney. Malfroy, B. and Schwartz, J. C., J. Biol. Chem. 259: 14365-14370 (1984); Gafford et al., Biochemistry 22: 3265-3271 (1983); and Pozsgay, M. et al., Biochemistry 25: 1292-1299 (1986). These studies indicate that enkephalinase preferentially hydrolyzes peptide bonds comprising the amino group of a hydrophobic residue, shows a marked preference for short peptides, and is most efficient when it acts as a dipeptidyl carboxypeptidase releasing a carboxy terminal dipeptide. Enkephalinase, which had been found in cerebral synaptic membranes, efficiently cleaves the $Gly^3$-$Phe^4$ amide of enkephalins (Malfroy, B. et al., Nature (Lond.) 276: 523-526 [1978]). Enkephalinase has also been found to cleave the heptapeptide ($Met^5$)enkephalin-$Arg^6$-$Phe^7$ (Schwartz, J. C. et al., In Proceedings International Union of Pharmacology 9th Congress of Pharmacology, 3: ed. by J. F. Mitchell et al., 277-283, McMillan Press Ltd., London, [1984]) as well as a variety of other neuropeptides, such as cholecystokinin (Zuzel, K. A. et al., Neuroscience 15: 149-158 [1985]), substance P (Horsthemke, B. et al. Biochem. Biophys. Res. Comm. 125: 728-733 [1984]), neurotensin (Checler et al., 1983), angiotensin I and angiotensin II (Matsas et al., Biochem J. 223: 433 [1984] and Gafford et al., Biochemistry 22: 3265 [1983]), kinins, e.g. bradykinin (Gafford, J. T. et al., Biochemistry 22: 3265-3271 [1983]), oxytocin (Johnson et al., 1984), and somatostatin (Mumford, R. A. et al., Proc. Natl. Acad. Sci. [U.S.A.] 78:6623-6627 [1981]). While enkephalinase is capable of hydrolyzing many biological peptides in vitro (Kenny, A. J. Trends in Biochem. Sci. 11: 40-42 [1986]), in vivo enkephalinase has to date only been implicated in the hydrolysis of endogenous enkephalins when released in brain (Schwartz, J. C. et al., Life Sciences 29: 1715-1740 [1981] and Lecomte, J. M. et al., J. Pharmacol. Exp. Ther. 237: 937-944 [1986]). Although the levels of enkephalinase in blood are normally very low (Connelly et al., supra) enkephalinase was found to be present in high levels in the serum from patients with adult respiratory distress syndrome (Connelly et al. Supra). Enkephalinase cleaves the chemotactic tripeptide fMet-Leu-Phe. Id. It was also observed that neutrophils from donors who smoked had enkephalinase activites about twice that of nonsmokers. Id. Enkephalinase has also been found in high levels in the microvilli of human placentae (Johnson, A. R. et al., Peptides 5: 789-796 [1984]).

Although the isolation of enkephalinase from various tissues has been described in the literature as shown above, the precise structure of enkephalinase has not been previously established. While some quantities of "purified" enkephalinase have been available as obtained from various tissues, the low concentration of enkephalinase in blood and tissues and the high cost, both economic and of effort, of purifying the protein from tissues makes this a scarce material. It is an object of the present invention to isolate DNA encoding enkephalinase and to produce useful quantities of human and mammalian enkephalinase using recombinant DNA techniques. It is a further object herein to prepare novel forms of enkephalinase. It is still another object herein to provide an improved substrate for the assay of enkephalinase activity. This and other objects of this invention will be apparent from the specification as a whole.

SUMMARY OF THE INVENTION

Objects of this invention have been accomplished by a method comprising: identifying and cloning the gene which codes for mammalian enkephalinase; incorporating that gene into a recombinant DNA vector; transforming a suitable host with the vector including that gene; expressing the mammalian enkephalinase gene in such a host; and recovering the mammalian enkephalinase that is produced. Similarly, the present invention makes it possible to produce human enkephalinase and/or derivatives thereof by recombinant techniques, as well as providing products and methods related to such human enkephalinase production. The isolation and identification of the enkephalinase gene was extremely difficult. The mRNA was rare and no cell line or other source of large quantities of mRNA was known, and heretofore no amino acid sequence for an enkephalinase was known.

The present invention is directed to the compositions and methods of producing mammalian enkephalinase via recombinant DNA technology, including: (1) the discovery and identity of the entire DNA sequence of the protein and the 5'-flanking region thereof; (2) the construction of cloning and expression vehicles comprising said DNA sequence, enabling the expression of the mammalian enkephalinase protein, as well as met, fusion or signal N-terminus conjugates thereof; and (3) viable cell cultures, genetically altered by virtue of their containing such vehicles and capable of producing mammalian enkephalinase polypeptide. This invention is further directed to compositions and methods of producing DNA which codes for cellular production of mammalian enkephalinase. Yet another aspect of this invention are new compounds, including deoxyribonucleotides and ribonucleotides which are utilized in obtaining clones which are capable of expressing enkephalinase. Still another aspect of the present invention is enkephalinase essentially free of all naturally occurring substances with which it is typically found in blood and/or tissues, i.e., the enkephalinase produced by recombinant means will be free of those contaminants typically found in its in vivo physiological milieu. In addition, depending upon the method of production, the enkephalinase hereof may contain associated glycosylation to a greater or lesser extent compared with material obtained from its in vivo physiological milieu, i.e. blood and/or tissue. This invention is further directed to novel enkephalinase derivatives, in particular derivatives lacking enkephalinase amino terminal residues, e.g. derivatives lacking the hydrophobic N-terminal amino acid sequence which constitutes the enkephalinase transmembrane domain.

The mammalian enkephalinase and derivatives thereof of this invention are useful in the treatment of various pathological disorders associated with various endogenous peptides such as the tachykinins, for example substance P, and the kinins, particularly bradykinin. The endogenous peptides may be associated with various pathological disorders including acute inflammation, hyperimmune responses e.g. anaphylaxis, tumors such as small cell lung cancer, carcinoid tumors, endocrine disorders, alterations in vascular permeability e.g. vasodilation attendant factor XII activation, and hypertension. Mammalian enkephalinase and its derivatives also are useful in diagnostic immunoassays for enkephalinase substrates such as bradykinin, wherein the enkephalinase serves to confirm the specificity of the assay for the substrate analyte by predigestion of an aliquot of the test sample. Finally, enkephalinase is useful as an immunosuppressant by virtue of its ability to digest chemotactic molecules. Other uses for enkephalinase will be apparent to those skilled in the art.

BRIEF DESCRIPTION OF THE DRAWINGS

FIG. 1 Nucleotide and amino acid sequence of human enkephalinase. The nucleotide sequence of the human enkephalinase mRNA was determined from DNA sequence analysis of a single clone. Predicted amino acids of the enkephalinase polypeptide are shown above the DNA sequence and are numbered from the first residue of the N-terminal of the analagous purified protein.

FIGS. 2a-2b FIGS. 2a-2b are collectively referred to herein as FIG. 2. Nucleotide and amino acid sequence of rat enkephalinase. The nucleotide sequence of the rat enkephalinase mRNA was determined from DNA sequence analysis of the cDNA clones λB16, λK3, λK5, λK2 and λB10 as shown in FIG. 2b. Predicted amino acids of the enkephalinase polypeptide are shown above the DNA sequence and are numbered from the first residue of the mature protein as determined by N-terminal protein sequencing. Alternate start codons are Met$^{-1}$ and Met$^{-8}$.

DETAILED DESCRIPTION

Figure 3:
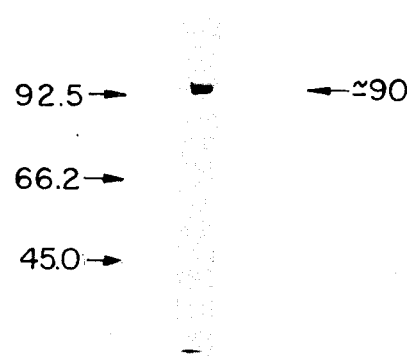
FIG. 3 SDS Polyacrylamide electrophoresis gel of purified rat kidney enkephalinase.
Figure 4:
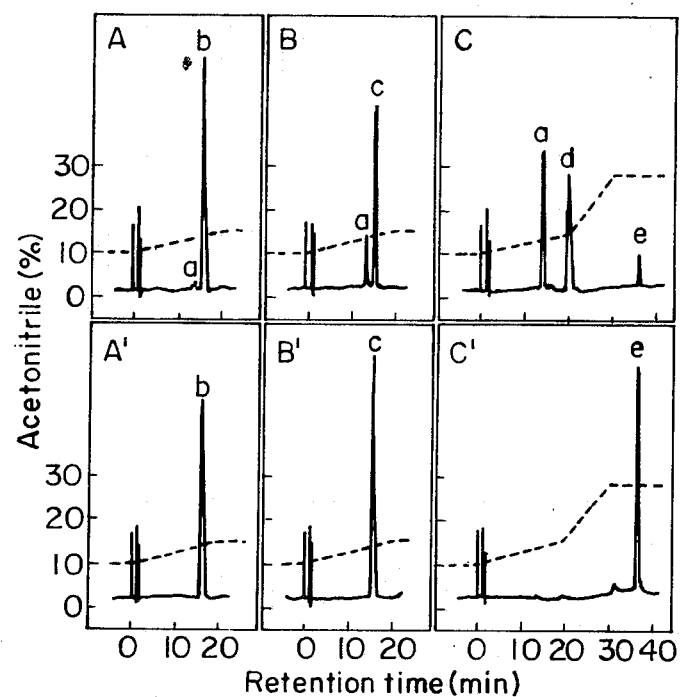
FIG. 4 HPLC analysis of the hydrolysis of tryptophan-containing peptides by purified rat kidney enkephalinase. The peptides (1 mM) were incubated for 1 hr at 37° C. with 5 ng purified rat kidney enkephalinase, without (A, B, C) and with A', B', C') 100 nM thiorphan. The substrates and fragments were resolved by reverse phase HPLC using a gradient of acetonitrile in 0.1% trifluoroacetic acid (dotted Line). A and A', Gly-Trp-Gly; B and B', N-Acetyl-Gly-Trp-Gly; C and C', dansyl-Gly-Trp-Gly. Peptides eluted are: a, Trp-Gly; b, Gly-Trp-Gly; c, N-Acetyl-Gly-Trp-Gly; d, dansyl-Gly; and e, dansyl-Gly-Trp-Gly.

As used herein, enkephalinase or enkephalinase derivatives refers to proteins which are enzymatically active or are immunologically cross-reactive with enzymatically active enkephalinase. Enzymatically functional enkephalinase is capable of cleaving the Gly$^3$-Phe$^4$ amide bond of $^3$H-(DAla$^2$, Leu$^5$)enkephalin in an assay as described by Llorens et al. (1982).

Included within the scope of enkephalinase as that term is used herein are enkephalinase having native glycosylation and the amino acid sequences of rat and human enkephalinase as set forth in FIG. 1 or 2, analogous enkephalinases from other animal species such as bovine, porcine and the like, deglycosylated or unglycosylated derivatives of such enkephalinases, amino acid sequence variants of enkephalinase and in vitro-generated covalent derivatives of enkephalinases. All of these forms of enkephalinase are enzymatically active or, if not, they bear at least one immune epitope in common with enzymatically-active enkephalinase.

Amino acid sequence variants of enkephalinase fall into one or more of three classes: Substitutional, insertional or deletional variants. These variants ordinarily are prepared by site specific mutagenesis of nucleotides in the DNA encoding the enkephalinase, thereby producing DNA encoding the variant, and thereafter expressing the DNA in recombinant cell culture. However, variant enkephalinase fragments having up to about 100–150 residues may be conveniently prepared by in vitro synthesis. Amino acid sequence variants are characterized by the predetermined nature of the variation, a feature that sets them apart from naturally occurring allelic or interspecies variation of the enkephalinase amino acid sequence. The variants typically exhibit the same qualitative biological activity as the naturally-occurring analogue, although variants also are selected in order to modify the characteristics of enkephalinase as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed enkephalinase variants screened for the optimal combination of desired activity. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. Obviously, the mutations that will be made in the DNA encoding the variant enkephalinase must not place the sequence out of reading frame and preferably will not create complementary regions that could produce secondary mRNA structure (EP 75,444A).

Substitutional variants are those in which at least one residue in the FIG. 1 or 2 sequences has been removed and a different residue inserted in its place. Such substitutions generally are made in accordance with the following Table 1 when it is desired to finely modulate the characteristics of enkephalinase.

TABLE 1

| Original Residue | Exemplary Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in enkephalinase properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A major class of substitutional or deletional variants are those involving the transmembrane and/or cytoplasmic regions of enkephalinase. The cytoplasmic domain of enkephalinase is the sequence of amino acid residues commencing at either of two alternative start codons shown in FIG. 2 (Met$^{-8}$ or Met$^{-1}$) or in FIG. 1 (beyond residue Lys$^{-5}$ or Met$^{-1}$) and continuing for approximately 21–24 additional residues. In the rat and human sequence the Pro-Lys-Pro-Lys-Lys-Lys domain (residues at about 8 through 13) is believed to serve as a stop transfer sequence; the conformational bends introduced by the prolyl residues and the electropositive character provided by the lysyl residues act, together with the transmembrane region described below, to bar transfer of enkephalinase through the cell membrane.

The transmembrane region of enkephalinase is located in the rat sequence at about residues 21–44 (where Asp is +1 as shown in FIG. 2), and in the human sequence at the analogous location. This region is a highly hydrophobic domain that is the proper size to span the lipid bilayer of the cellular membrane. It is believed to function in concert with the cytoplasmic domains to anchor enkephalinase in the cell membrane.

Deletion or substitution of either or both of the cytoplasmic and transmembrane domains will facilitate recovery of recombinant enkephalinase by reducing its cellular or membrane lipid affinity and improving its water solubility so that detergents will not be required to maintain enkephalinase in aqueous solution. Deletion of the cytoplasmic domain alone, while retaining the transmembrane sequence, will produce enkephalinase which would be solubilized with detergent but which offers therapeutic advantages. The cytoplasmic domain-deleted enkephalinase will be more likely to insert into all membranes when administered as a therapeutic, thereby targeting its activity to the immediate extracellular envelope in which it is ordinarily active, and would improve its solubility in salve or liposomal compositions containing hydrophobic micelles. Preferably, the cytoplasmic or transmembrane domains are deleted, rather than substituted (for example [Ser]$_6$ for the stop transfer sequence), in order to avoid the introduction of potentially immunogenic epitopes.

The cytoplasmic and/or transmembrane (C-T) deleted or substituted enkephalinase can be synthesized directly in recombinant cell culture or as a fusion with a signal sequence, preferably a host-homologous signal. For example, in constructing a procaryotic expression vector the C-T domains are deleted in favor of the bacterial alkaline phosphatase, lpp or heat stable enterotoxin II leaders, and for yeast the domains are substituted by the yeast invertase, alpha factor or acid phosphatase leaders. In mammalian cell expression the C-T domains are substituted by a mammalian cell viral secretory leader, for example the herpes simplex gD signal. When the secretory leader is "recognized" by the host, the host signal peptidase is capable of cleaving a fusion of the leader polypeptide fused at its C-terminus to C-T deleted enkephalinase. The advantage of C-T deleted enkephalinase is that it is capable of being secreted into the culture medium. This variant is water soluble and does not have an appreciable affinity for cell membrane lipids, thus considerably simplifying its recovery from recombinant cell culture.

Substitutional or deletional mutagenesis is employed to eliminate N- or O-linked glycosylation sites. Alternatively, unglycosylated enkephalinase is produced in recombinant prokaryotic cell culture. Deletions of cysteine or other labile residues also may be desirable, for example in increasing the oxidative stability of the enkephalinase. Deletions or substitutions of potential proteolysis sites, e.g. Arg Arg, is accomplished by deleting one of the basic residues or substituting one by glutaminyl or histidyl residues.

Insertional amino acid sequence variants of enkephalinases are those in which one or more amino acid residues are introduced into a predetermined site in the target enkephalinase. Most commonly, insertional variants are fusions of heterologous proteins or polypeptides to the amino or carboxyl terminus of enkephalinase. Immunogenic enkephalinase derivatives are made by fusing an immunogenic polypeptide to the target sequence by crosslinking in vitro or by recombinant cell culture transformed with DNA encoding the fusion. Such immunogenic polypeptides preferably are bacterial polypeptides such as trpLE, beta-galactosidase and the like, together with their immunogenic fragments.

DNA encoding enkephalinase is obtained from other sources than rat or human by (a) obtaining a cDNA library from the kidney of the particular animal, (b) conducting hybridization analysis with labelled DNA encoding human enkephalinase or fragments thereof (usually, greater than 100 bp) in order to detect clones in the cDNA library containing homologous sequences, and (c) analyzing the clones by restriction enzyme analysis and nucleic acid sequencing to identify full-length clones. If full length clones are not present in the library, then appropriate fragments may be recovered from the various clones and ligated at restriction sites common to the clones to assemble a full-length clone.

Enkephalinase derivatives that are not enzymatically active which fall within the scope of this invention include polypeptides that may or may not be substantially homologous with enkephalinase. These enkephalinase derivatives are produced by the recombinant or organic synthetic preparation of enkephalinase fragments or by introducing amino acid sequence variations into intact enkephalinase so that it no longer demonstrates enzyme activity as defined above. Only those non-enzymatically active enkephalinases or derivatives which exhibit immunological cross reactivity are included within the scope hereof.

Immunologically cross-reactive means that the candidate polypeptide is capable of competitively inhibiting the binding of an enzymatically-active enkephalinase with polyclonal antisera raised against the enzymatically-active analogue. Such antisera are prepared in conventional fashion by injecting goats or rabbits subcutaneously with the enzymatically-active analogue in complete Freund's adjuvant, followed by booster intraperitoneal or subcutaneous injections in incomplete Freunds.

Enkephalinase derivatives that are not enzymatically active but which are capable of cross-reacting with antisera to enzymatically-active enkephalinase are useful (a) as a reagent in diagnostic assays for enkephalinase or antibodies to enkephalinase, (b) when insolubilized in accord with known methods, as agents for purifying anti-enkephalinase antibodies from antisera or hybridoma culture supernatants, and (c) as immunogens for raising antibodies to enzymatically-active enkephalinase.

"Essentially free from" or "essentially pure" when used to describe the state of enkephalinase produced by the invention means free of protein or other materials normally associated with enkephalinase in its in vivo physiological milieu as for example when enkephalinase is obtained from blood and/or tissues by extraction and purification. Enkephalinase produced by the method of the instant invention was greater than or equal to 95% enkephalinase by weight of total protein; constituted a single saturated band (by Coomasie blue staining) on polyacrylamide gel electrophoresis; and had a specific activity of at least about 25 nmole/mg protein/min. using 20 nM of $^3$H-(DAla$^2$,Leu$^5$)enkephalin as substrate at 25° C. in 50 mM pH 7.4 HEPES buffer containing 0.02% Tween 20.

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting.

Prokaryotes also are used for expression. The aforementioned strains, as well as E. coli W3110 (F$^-$, $\lambda^-$, prototrophic, ATCC No. 27325), bacilli such as Bacillus subtilus, and other enterobacteriaceae such as Salmonella typhimurium or Serratia marcescans, and various pseudomonas species may be used.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, E. coli is typically transformed using pBR322, a plasmid derived from an E. coli species (Bolivar, et al., Gene 2: 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., "Nature", 275: 615 [1978]; and Goeddel et al., "Nature" 281: 544 [1979]), alkaline phosphatase, the tryptophan (trp) promoter system (Goeddel "Nucleic Acids Res." 8: 4057 [1980] and EPO Appln. Publ. No. 36,776) and hybrid promoters such as the tac promoter (H. de Boer et al., "Proc. Natl. Acad. Sci. U.S.A." 80: 21-25 [1983]). However, other functional bacterial promoters are suitable. Their nucleotide sequences are generally known, thereby enabling a skilled worker operably to ligate them to DNA encoding enkephalinase (Siebenlist et al., "Cell" 20: 269 [1980]) using linkers or adaptors to supply any required restriction sites. Promoters for use in bacterial systems also will contain a Shine-Dalgarno (S.D.) sequence operably linked to the DNA encoding enkephalinase.

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in Saccharomyces, the plasmid YRp7, for example, (Stinchcomb, et al., Nature 282: 39 [1979]; Kingsman et al, Gene 7: 141 [1979]; Tschemper et al., Gene 10: 157 [1980]) is commonly used. This plasmid already contains the trpl gene which provides a selection marker for a mutant strain of yeast lacking the ability to grow in tryptophan, for example ATCC no. 44076 or PEP4-1 (Jones, Genetics 85: 12 [1977]). The presence of the trpl lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al., "J. Biol. Chem." 255: 2073 [1980]) or other glycolytic enzymes (Hess et al., "J. Adv. Enzyme Reg." 7: 149 [1968]; and Holland, "Biochemistry" 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the transcribed mRNA.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful herein.

Transcription of a DNA encoding enkephalinase by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, L. et al., PNAS 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding enkephalinase. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of evergreater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the vectors of this invention encoding enkephalinase in higher eukaryotes include: monkey kidney CV1 line transformed by SV40 (COS-7, ATCC CRL 1651); human embryonic kidney line (293, Graham, F. L. et al. J. Gen. Virol. 36: 59 [1977]); baby hamster kidney cells (BHK, ATCC CCL 10); chinese hamster ovary-cells-DHFR (CHO, Urlaub and Chasin, PNAS (U.S.A.) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44–68 [1982]).

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (U.S.A.), 69: 2110 (1972).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform E. coli K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinary skilled artisan.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

An assay using novel fluoroescent substrates for enkephalinase was developed to assess whether enkephalinase is expressed. This assay is based on the disappearance of energy transfer between a tryptophan or a tyrosine residue and the 5-dimethylaminonaphthalene-1-sulfonyl group (dansyl) in the substrates dansyl-Gly-Trp-Gly or dansyl-Gly-Tyr-Gly upon hydrolysis of their Gly-Trp or Gly-Tyr amide bond by enkephalinase. No significant difference in Km or kcat values were found for dansyl-Gly-Trp-Gly and dansyl-Gly-Tyr-Gly as the active site of enkephalinase appears to accommodate tryptophan residues similarly to tyrosine. The tryptophan and tyrosine containing substrates can be used for continuous recording of enkephalinase activity.

In order to faciliate understanding of the following examples certain frequently occurring methods and/or terms will be described.

"Plasmids" are designated by a lower case p preceded and/or followed by capital letters and/or numbers. The starting plasmids herein are either commercially available, publicly available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning* pp. 133-134 (1982). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

Enkephalinase and its recombinant expression product is obtained according to the following protocol:

1. Rat kidney enkephalinase was purified to apparent homogeneity.
2. The N-terminal amino acid sequence of enkephalinase was determined.
3. Purified enkephalinase was digested with Lysine C-proteinase. The peptides generated were resolved using HPLC over a $C_4$ reverse phase column, and those peptides having a high absorbance at 280 nm were sequenced.
4. Oligonucleotide probes corresponding to a tryptophan-rich-containing peptide fragment were chemically synthesized.
5. cDNA libraries were constructed in λgt10, using (a) randomly primed polyA+ enriched mRNA from rat kidney, (b) oligo dT primed polyA+ enriched mRNA from rat brain, (c) oligo dT primed polyA+ enriched mRNA from rat kidney and (d) oligo dT primed polyA+ enriched mRNA from human placenta.
6. A pool of radiolabeled synthetic deoxyoligonucleotides complementary to codons for amino acid sequences of enkephalinase were used, as described below, such as:
    (a) 5' GAA GTT GTT GGC GGA CTG CTG GGT CCA CCA GTC GAC CAG GTC GCC
    (b) 5' XTG XTG YGT CCA CCA ZTC 3'
    X=T or C
    Y=G, A, T, or C
    Z=Z or G
7. The randomly primed rat kidney library was screened using the chemically synthesized oligonucleotide long and short probes labelled using polynucleotide kinase and =P-ATP. Double positive plaques were purified and inserts sequenced.
8. One =P labelled insert was used to rescreen the oligo dT primed rat brain and rat kidney libraries.
9. The complete reading frame for enkephalinase was obtained from two overlapping clones. The cDNA from kidney and brain were identical as determined by DNA sequence analysis of the clones obtained.
10. The human placental library was screened using a =P-labelled partial clone from the rat cDNA. A full length clone, as determined by comparision to the rat cDNA, was isolated and sequenced.
11. A full length cDNA encoding rat enkephalinase was constructed from two overlapping clones in a plasmid and sequenced. It should be appreciated that disclosure of the DNA sequence in FIGS. 1 and 2 enables one to prepare extremely long probes having perfect homology with rat or human enkephalinase cDNA, thereby considerably simplifying and increasing the efficiency of probing cDNA or genomic libraries from these or other species, and making it possible to dispense with enkephalinase purification, sequencing, and the preparation of probe pools.
12. The full length cDNA encoding human enkephalinase was then tailored into an expression vehicle which was used to transform an appropriate host cell, which was then grown in a culture to produce the desired enkephalinase.
13. Biologically active mature enkephalinase produced according to the foregoing procedure has two alternative amino termini as shown in FIG. 2 which result in embodiments having 742 or 749 amino acids.

The following examples merely illustrate the best mode now known for practicing the invention, but should not be construed to limit the invention. All literature citations herein are expressly incorporated by reference.

EXAMPLE 1

Purification or Rat Kidney Enkephalinase

All the operations described below were performed at 40° C. The proteins were measured by the method of Bradford, M. M., Anal. Biochem. 72: 248-254 (1976) using bovine serum albumin as standard. The purification scheme adopted in this study was adapted from that of Malfroy and Schwartz, J. Biol. Chem. 259: 14365-14370 (1984) as follows:

The kidneys from sixty male rats (200-250 g) were removed and immediately frozen and stored at −20° C. until use.

Solubilization

The kidneys were thawed on ice, and homogenized into 1 liter of ice-cold HEPES (N-2-hydroxyethylpiperazine-N'-2'-ethanesulfonic acid)/NaOH buffer (50 mM, pH 7.4) using a Polytron homogenizer (5 minutes at maximal speed using the large probe of the homogenizer). The homogenate was centifuged at 20,000 g for 30 minutes, the pellet resuspended using the Polytron homogenizer into 1 liter of the same buffer, and the suspension centrifuged again at 20,000 g for 30 minutes. The resulting pellet was then resuspended into 500 ml of the above buffer containing 0.1% Triton X-100, and left at 4° C. under constant magnetic stirring for 4 hours.

The suspension was centrifuged at 20,000 g for 1 hour, the supernatant discarded and the pellet resuspended into 500 ml of the above buffer, containing 1% Triton X-100 and left at 4° C. under magnetic stirring for 16 hours.

The suspension was centrifuged at 40,000 g for 1 hour, and the supernatant containing the solubilized enzyme was kept for further use. All the centrifugations were performed in a Sorvall RC-5B centrifuge, equipped with a GSA rotor, and a SS-34 rotor for the last step.

Concanavalin-A Chromatography

The solubilized preparation was loaded onto a 26×50 mm Concanavalin-A sepharose column (Pharmacia), equilibrated with 5 mM pH 7.74 HEPES buffer containing 0.1% Triton X-100, at a flow rate of 100 ml/h. The column was washed with 500 ml of the above buffer, and the enzyme was eluted with 200 ml of buffer containing 500 mM methyl-alpha-D-glucopyranoside. This last fraction containing the enzyme was then subjected to DEAE Sephadex chromatography.

DEAE Sephadex A-50 Chromatography

The foregoing fraction eluted from the Concanavalin-A column was loaded at a flow rate of 100 ml/h onto a 16×100 mm DEAE Sephadex A-50 (Pharmacia) column previously equilibrated in 5 mM, pH 7.4 HEPES buffer, containing 0.1% Triton X-100. After an initial wash with 200 ml of the same buffer, the column was eluted at a flow rate of 50 ml/h with a 1 liter linear gradient of 0 to 250 mM NaCl in the same buffer. Fractions of ten ml were collected.

Hydroxylapatite Chromatography

The fractions containing enkephalinase activity absent of detectable angiotensin-converting enzyme (ACE) activity (as described by the method described by Malfroy, B. and Schwartz, J. C., J. Biol. Chem. 259: 14365–14370 [1984]) were pooled and loaded at a flow rate of 30 ml/h onto a 10×50 mm hydroxylapapite column (BioRad) preequilibrated in 5 mM, pH 7.4 HEPES buffer, containing 0.1% Triton X-100. The column was eluted at a flow rate of 20 ml/hr. with a 400 ml linear gradient of 0 to 250 mM phosphate/Na ions in the above buffer. Fractions of eight ml were collected.

Concentration on Concanavalin-A Sepharose

The fractions eluted from hydroxypatite containing enkephalinase activity were pooled and loaded at a flow rate of 10 ml/h onto a 10×10 mm Concanavalin-A sepharose column previously equilibrated with 5 mM, pH 7.4 Hepes buffer. The column was washed several times to dryness, i.e. until all buffer was absent, with the aforementioned buffer until no Triton X-100 could be detected in the eluate using the Bradford (1976) protein assay; then with the same buffer containing 500 mM methyl-alpha-D-glucopyranoside; and then several times with 1 ml 5 mM, pH 7.4 HEPES buffer containing 500 mM methyl-alpha-D-glucopyranoside and 0.1% Triton X-100, at a flow rate of 5 ml/h.

Superose Chromatography

One ml fractions obtained from the previous concanavalin-A step were concentrated to 200 μl using Centricon 30 devices and loaded onto a Superose-12 column (Pharmacia) equilabrated with 100 mM, pH 7.4 phosphate/Na buffer containing 1% SDS and 100 mM dithiothreitol. The column was eluted with the same buffer at a flow rate of 250 μl/min. Five hundred μl fractions were collected.

In another set of experiments, a Superose-6 column was used and run in 5 mM phosphate/Na buffer containing 150 mM NaCl and 0.1% Triton X-100, a buffer which allowed subsequent measurement of enkephalinase activity.

Assay of Enkephalinase Activity

Enkephalinase activity was measured as described by Llorens et al. (1982) using $^3$H-(DAla$^2$, Leu$^5$)enkephalin as a substrate. The buffer used was 50 mM, pH 7.4 Hepes, containing 0.02% Triton X-100.

Amino Acid Sequence Analysis

The fractions eluted from the Superose-6 column, containing enkephalinase activity and displaying a single protein band on polyacrylamide gels stained with coomassie blue, were used for sequence analysis. Enkephalinase was digested with Lysine-C proteinase in a ratio of 100 ng of proteninase for each 1 μg of enkephalinase. The peptide fragments generated were separated by HPLC on a Synchrom 2×100 mm C$_4$ column, eluted with a linear gradient of 1 to 70% propanol-1 (1% per min) in 0.1% trifluoroacetic acid at a flow rate of 400 μl per minute. Peptides were detected by their absorbance at 214 and 280 nm. Sequential Edman degradation was performed on an Applied Biosystem, model 470A sequencer equipped with an on line model 120 PTH analyzer.

Six 1 ml fractions from the last Concanavalin-A step were collected and analyzed. The fractions contained a total of 525 μg protein, and enkephalinase activity at a specific activity of 27.4 nmole/mg protein/min, when measured at 25° C., using $^3$H-(DAla$^2$, Leu$^5$)enkephalin as a substrate. A 7.5% polyacrylamide SDS gel electrophoresis (FIG. 3) showed the presence of a 90 Kdalton protein, and of an approximately 50 Kdalton protein that was much less abundant. These two proteins could be easily separated by an additional chromatographic step on a Superose-6 or Superose-12 column. Only those fractions eluted from the Superose columns that contained the 90 Kdalton protein, also contained enkephalinase activity. This demonstrates that, in agreement with many previous reports, the molecular weight of enkephalinase is about 90 Kdaltons (for review see Kenny, cited above.) Fractions eluted from the Superose columns, and completely devoid of the 50 Kdalton contaminant protein, were used for protein sequencing.

Table 2 shows the N-terminal amino acid sequence. Sequencing was not extended over 15 cycles because the yields obtained were to low. The large size of enkephalinase could account for this difficulty.

TABLE 2

SEQUENCE ANALYSIS OF INTACT ENKEPHALINASE

| Cycle | Amino Acid | Yield (pmole) |
|---|---|---|
| 1 | (Asp) | 23.7 |
| 2 | Ile | 7.6 |
| 3 | Thr | 7.8 |
| 4 | Asp | 11.3 |
| 5 | Ile | 6.0 |
| 6 | Asn | 6.3 |
| 7 | Ala | 8.7 |
| 8 | Pro | 5.2 |
| 9 | Lys | 3.4 |
| 10 | Pro[a] | — |
| 11 | Lys[a] | — |
| 12 | Lys[a] | — |
| 13 | Lys[a] | — |
| 14 | Gln[a] | — |
| 15 | Arg[a] | — |

[a]Identified but not quantitated.

Other protein sequence data summarized in Table 3, were obtained after Lysine-C proteinase digest of enkephalinase, and HPLC purification of some of the peptides that were generated.

TABLE 3

| Peptide | Sequence (in order of cycle) |
|---|---|
| KC8 | (Leu) Leu Pro Gly Leu Asp Leu Asn His Lys |
| KC31 | (N.I.) Ile Thr Asp Ile Asn Ala Pro Lys Pro Lys[a] |
| KC2-12-6 | Glu Arg Ile Gly Tyr Pro Asp Asp Ile Ile Ser Asn - Glu Asn Lys |
| KC2-18-4 | (N.I.) Gly Asp Leu Val Asp Trp Trp Thr Gln Gln - Ser Ala Asn Asn Phe Lys[a] |
| KC2-19 | Glu Glu Glu Tyr Phe Glu Asn Ile Ile Gln Asn Leu Lys |
| KC2-32 | Ala Val Val Glu Asp Leu Ile Ala Gln Ile Arg Glu - Val Phe Ile Gln Thr Leu |

N.I. = not identified
[a]Identified but not quantitated

EXAMPLE 2

Enkephalinase DNA

Messenger RNA Isolation

Total RNA from rat kidney and brain was extracted by the guanidine thiocyanate method (Kaplan, B. B. et al., Biochem. J. 183, 181–4[1979]) and CsCl ultracentrifugation. The general strategy followed for identification of clones containing coding sequences for enkephalinase was as follows:

1. High complexity cDNA libraries were constructed in λgt10.
2. Both short and long probes were prepared.
3. cDNA clones were screened using both long and short probes and double positive plaques were isolated.

Library Construction

Polyadenylated mRNA was prepared from freshly obtained and liquid $N_2$ frozen rat kidneys (Kaplan et al., Biochem. J. 183:181–184 [1979]). High complexity cDNA libraries were constructed in λgt10 (Huynh et al., *DNA Cloning Techniques*, D. Clover, Ed., [1984]).

A rat kidney cDNA library was prepared using 5 μg polyA+ mRNA primed with either random octamer primers or with oligo dT primers. All cDNA libraries were constructed as described by Wood et al., Nature 312:330–337 (1984) except that the adaptors used had the sequence

5'-AATTCACTCGAGACGC-3'
3'GTGAGCTCTGCG-5'P.

This adaptor is referred to as EcoRI-XhoI. Other adaptors used were:

5'-AATTCGCATGGTCGACTAC-3'
      GCGTACCAGCTGATG-5'P referred to as EcoRI-SalI:

5'-AATTCCTCGTGCTTCT-3'
      GGAGCACGAAGA-5'P referred to as EcoRI.

In the case of the randomly primed library using the EcoRI-XhoI adaptor $6 \times 10^6$ independent isolates of greater than 500 bp were obtained. In the case of the oligo dt primed library using an EcoRI adaptor $7 \times 10^5$ isolates of greater than 1500 bp were obtained.

The foregoing procedure was followed for the preparation of a cDNA library from rat brain. An oligo dT primed library using an EcoRI-XhoI adaptor yielded $6 \times 10^6$ independent isolates of greater than 1500 bp.

A similar procedure was followed for the preparation of a cDNA library from human placenta. An oligo dT primed library using an EcoRI-SalI adaptor $7 \times 10^5$ independent isolates of greater than 1500 bp. This library has previously been demonstrated to contain many full length cDNA clones (Ullrich, A. et al., 1985, Nature 313:756–761).

Preparation of DNA probe

A total of seven lysine-C peptides were sequenced (Table 3) as well as the amino terminus (Table 2). Peptide KC2-18-4 containing two tryptophan residues was chosen to design oligonucleotide probes. A first probe (short probe) was a mixture of 18-mers that covered all the possible nucleotide sequences complementary to a gene coding for Asp-Trp-Trp-Thr-Gln-Gln, i.e. a mixture of 32 18-mers, as shown below:

| | | Asp—Trp—Trp—Thr—Gln—Gln | |
|---|---|---|---|
| coding strand: | 5' | GAX—TGG—TGG—ACY—CAA | 3' |
| complementary: | 5' | XTG—XTG—YGT—CCA—CCA—ZTC | 3' |

X = T or C
Y = G, A, T, or C
Z = G or A

A second probe (long probe), complementary to a coding strand for the entire peptide KC2-18-4 (excluding the terminal Lys) was also used:

5' GAA GTT GTT GGC GGA CTG CTG GGT CCA CCA GTC GAC CAG GTC GCC 3'.

The oligonucleotide probes were labelled with =P using nucleotide kinase (Maniatis et al., Molecular Cloning, A Laboratory Manual [Cold Spring Harbor Laboratory, 1982]) and used to screen $5 \times 10^5$ clones from a λgt10 library constructed by random-priming poly A-enriched rat kidney RNA. The library was plated at a density of 25,000 plaques per plate, lifted twice on nitrocellulose filters and the DNA on the filters was denatured and fixed as described by Maniatis et al. (1982).

The filters were prehydridized for 4 hours at room temperature in 50 mM sodium phosphate pH 6.8, 5× SSC (Blin et al., Nucleic Acids Res. 3:2303 [1976]), 150 mg/ml sonicated salmon sperem DNA, 5× Denhardt's solution (Wahl et al., Proc. Nat. Acad. Sci. [U.S.A.] 76:3683 [1979]) 20 percent formamide and then hybridized with $50 \times 10^6$ counts per minute of the labelled probes in the same solution. After an overnight incubation at room temperature, the filters were washed in 5xSSC, 0.1% SDS. The filters incubated with the long probe were then washed several times in 0.5xSSC, 0.1% SDS at room temperature. The filters incubated with the short probes pool were washed in 2xSCC containing 3M tetramethyl ammonium chloride (Wood et al., Proc. Natl. Acad. Sci. U.S.A., 82: 1585–1588 [1985]) at 51° c. for 45 min., then in 2xSSC at room temperature for 1 hour. Filters were then exposed to Kodak XR-5 X-ray films with Dupont Lightning Plus intensifying screens for 16 hours at −70° C.

Two positive λgt10 phage were isolated and designated λK3 and λK4. The inserts of these were subcloned into M13 derivatives (Messing et al., "Nucl. Acids. Res." 9:309–321 [1981]) and sequenced by the dideoxy chain termination method of Sanger et al., Proc. Natl. Acad. Sci. U.S.A. 74:5463–5467 (1977).

This analysis revealed that neither of the characterized cDNAs contained sufficient sequence information to predict the complete structure of the protein. However, they did code for DNA comprising the peptide sequence of KC2-18-4. Therefore, rat kidney and rat brain oligo-dT primed libraries were screened.

The rat kidney library was screened with a suitable restriction fragment (both EcoRI fragments of λK3) from a previously analyzed cDNA and yielded several isolates (λK2 and λK5) of which none specified the remainder of the DNA sequences encoding the N-terminal region.

Similar screening of the rat brain library however gave two clones (λB16 and λB10), one of which, λB16, contained the N-terminal portion of the cDNA.

Completeness of the rat coding sequence was assessed from the presence of a long open reading frame which specified the sequence (as shown in FIG. 2) beginning with a start codon and preceded by an in-frame stop codon. An additional start codon is located 8 codons downstream. As noted, two possible inititation codons are present and either may be used. However, the N-terminal protein sequence suggests that the second start codon is actually used in vivo. Neither AUG codon conforms closely to the Kozak rule for prediction of initiation codons (Kozak, M., 1986, Cell 44: 283–291).

The cDNA inserts (see FIG. 2) were demonstrated to be the DNA coding for enkephalinase by comparing the amino acid sequence encoded by the cDNA with the peptide sequence, as described above, obtained from purified enkephalinase. The cDNA insert of these clones contains 912 bp of the 3' untranslated sequence and 78 bp at the 5' untranslated region.

At position 1917 in the rat DNA sequence, λB10 and λK2 have a T (coding for Asn). However, in λK3 a C was detected. This does not change the coding potential of the cDNA. Also, in the 3' untranslated sequence, position 2930 is a G in λK2 and an A in λB10. These different nucleotides may reflect a reverse transcriptase error.

Despite screening high complexity rat kidney and brain cDNA libraries, none yielded any full length cDNA's. This hampered initial screenings based on the use of two separate long probes such as those based on peptide sequences KC2-19 and KC2-32. Also the N-terminal probe was never found to be effective due to incorrect codon choices being made at the stage of design of the oligonucleotide. Screening with the KC2-18-4 short probe alone also was not successful in allowing isolation of positive clones because of the many false positives that were obtained with its use. Isolation of complete enkephalinase cDNA required dual screening with both long and short probes, whereas the typical procedure heretofore has been to use either screening method alone.

Human Enkephalinase cDNA

The cDNA insert of λK3 was used to screen $1.6 \times 10^6$ human placental cDNA clones as described above. Five positive clones were obtained, and two were sequenced. The largest insert obtained was three and a half Kilobases and yielded nearly a full length cDNA. As shown in FIG. 1, the entire human enkephalinase cDNA has been obtained based on the N-terminus of purified native enkephalinase. The predicted protein is greater than 90% homologous to the rat cDNA with several non-conservative changes being observed (French, S. and Robson, B., 1983, J. Mol. Evol. 19: 171–175).

At position 1413 in the human DNA sequence, one clone λH7 was observed to have a G. This codes for an Ala residue as shown in FIG. 1. However in a different clone λH5 this nucleotide is an A. This would change the codon to a Thr. Since the former is identical to the rat amino acid at position 465, the latter probably represents and error of reverse transcriptase synthesis of the mRNA.

EXAMPLE 3

Expression of Rat Enkephalinase

Partial cDNA clones encoding rat enkephalinase were obtained. Fusion of the appropriate fragments to construct a full length cDNA was undertaken as follows.

The M13 sequencing derivatives of λB16 and the 3' end of λK5 were used for these constructions. The full length λB16 insert was subcloned by digestion of the SalI sites in the adaptor and ligated to SalI cleaved M13tg130 for sequencing. This phage ss16X.1 was converted to double stranded DNA by primer extension (using the M13 universal sequencing primer and DNA polymerase) and digested with HindIII. HindIII cleaves the phage in the polylinker region 5' of the initiation codon. The HindIII site was blunted using T4 DNA polymerase. The plasmid was then digested with BglII (which is a unique site in rat enkephalinase located at position 1173) and the approximately 1190 bp HindIII (blunted)-BglII fragment isolated (fragment 1). The approximately 1380 bp EcoRI fragment of λK5, extending from the adaptor sequence located adjacent to position 1189 in rat enkephalinase, and going 3' for 1268 bp to the EcoRI site in the adaptor was subcloned into M13mp19 for sequencing. This phage ssP5.1 was converted to double stranded DNA by primer extension, digested with EcoRI, blunt ended using T4 DNA polyperase and then digested with BglII. The approximately 1290 bp BglII-EcoRI (blunted) fragment was isolated (fragment 2).

Fragments 1 and 2 were ligated (in 10 mM rATP, which inhibits blunt-end ligation) and the approximately 2480 bp product (1190 bp + 1290 bp = 2480 bp) eluted from the gel. This approximately 2480 bp product was ligated to SmaI digested pSP64 (Melton, D. A.

et al., Nucleric Acids Res. 12:7035-56 [1984]). This construct (p Rat. enk. antisense i.e. prENKanti) containing a full length rat enkephalinase was sequenced. prENKanti was cleaved with HindIII and SacI (both of these unique sites occur in the polylinker region of the pSP64 vector). This approximately 2520 kb fragment is then used in the following procedure.

(A) The fragment is ligated to pSP65 (Melton et al., Id.) cleaved with HindIII and SacI. The resultant plasmid prENKsense is used to generate in vitro transcription/translation product (using SP6 polymerase [Promega Biotech]) and rabbit reticulocyte lysate (Promega Biotech). This in vitro translated material is assayed for enkephalinase activity.

(B) The 2520 Kb fragment is blunted with T4 DNA polymerase and ligated to the pCIS2.8C28D described in U.S. patent application Ser. No. 06/907,297 which is hereby incorporated by reference which has been cleaved with ClaI and HpaI and blunted. pCIS2.8C28D is the same vector as pCIStPA, described below, except that it contains a factor VIII derivative instead of tPA. A recombinant plasmid pCISrENK was isolated in which the 5' end of the rat cDNA is located next to the CMV promoter enhancer region. This plasmid is expressed in human embryonic kidney (293) cells as described (see Example 4) and purified.

EXAMPLE 4

Expression of Human Enkephalinase

Figure 7:
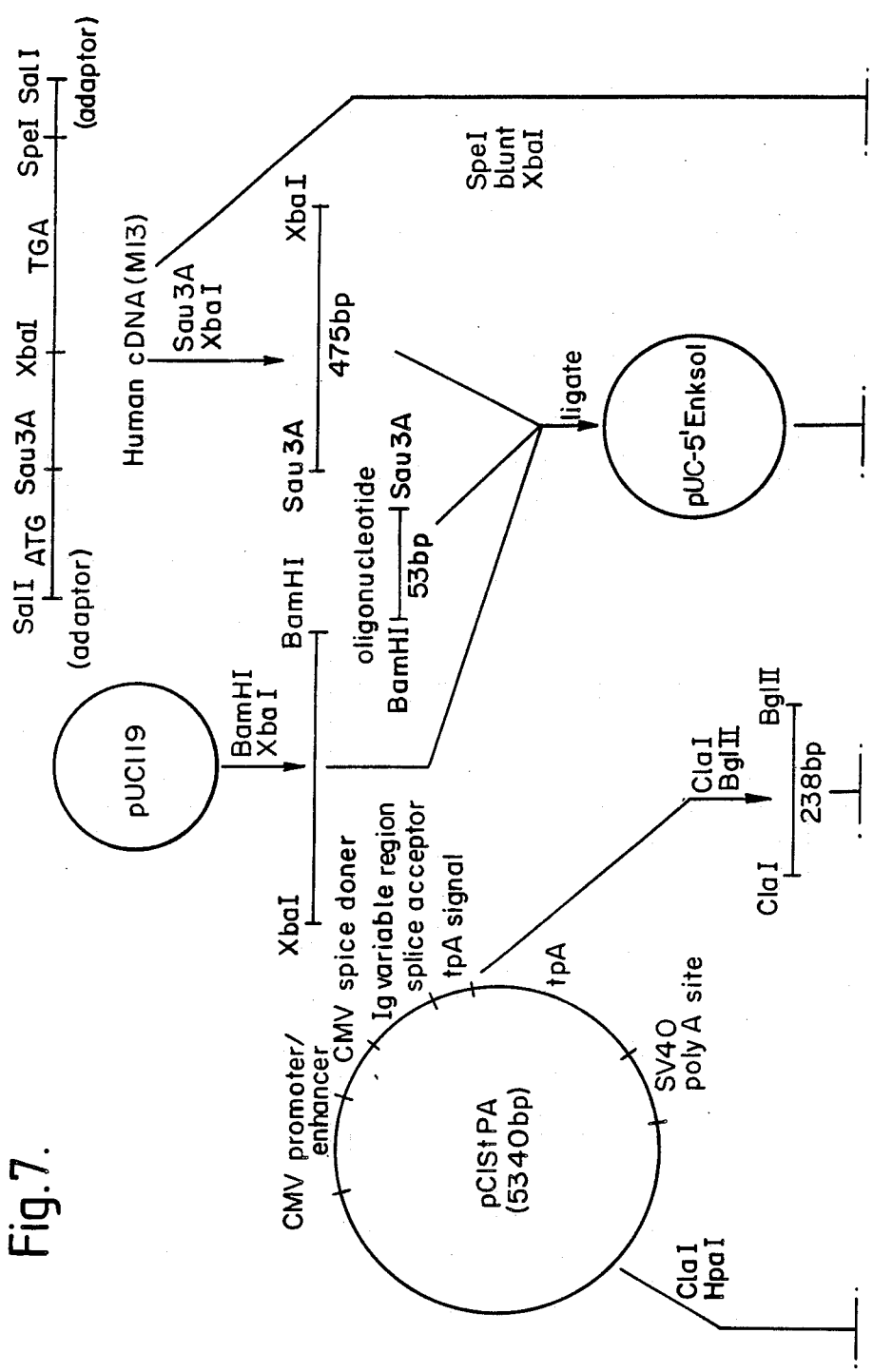
FIG. 7 A contemplated procedure for the construction of expression vectors for human enkephalinase deletional variants.
Figure 7:
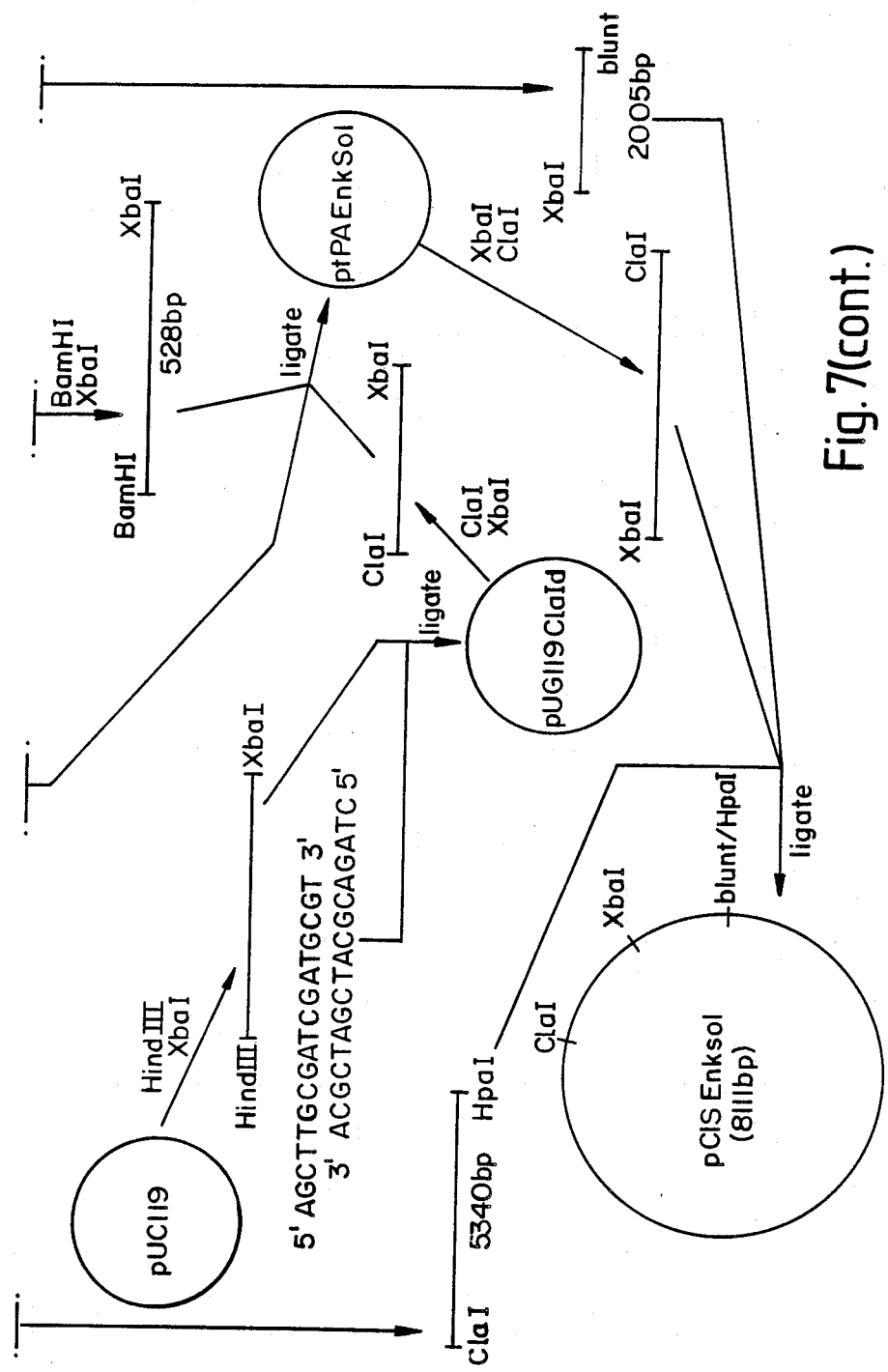

These procedures are concerned with the construction of vectors containing the cytomegalovirus enhancer and promoter, the cytomegalovirus splice donor site and intron, the Ig variable region splice acceptor site, the SV40 polyadenylation and transcription site and cDNA encoding either cytoplasmic domain-deleted or cytoplasmic plus transmembrane (C-T) domain-deleted enkephalinase, either of which were ligated at their 5' ends to the tissue plasminogen activator secretion signal. The construction of the C-T deleted variant is shown in FIG. 7.

Cytoplasmic-Transmembrane Domains Deleted Enkephalinase (1) A 475 bp fragment is isolated from the full length human cDNA, described above, by digestion with Sau3A and XbaI. A 53mer is chemically synthesized having the following sequence:

```
5'-GA TCC GGT ATT TGC AAG TCA TCA GAC TGC ATA AAA TCA GCT GCT CGA CT      3'
3'      G CCA TAA ACG TTC AGT AGT CTG ACG TAT TTT AGT CGA CGA GCT GAC TAG-5'.
```

This 53mer will comprise the amino terminus of the C-T deleted enkephalinase. The plasmid pUC119 (see for example U.S. patent application Ser. No. 06/907,297, which is hereby incorporated by reference) was digested with BamHI and XbaI. (In this regard, pUC19 can be employed in place of pUC119.) A three part ligation is then carried out. The 53mer is ligated to the 475 bp fragment and then the 528 bp fragment is cloned into pUC119 at the BamHI and XbaI sites. This intermediate plasmid, labelled pUC-5' Enksol, was sequenced to confirm proper orientation of the inserts.

(2) pCIStPA (see U.S. patent application Ser. No. 06/907,185 which is hereby incorporated by reference) cloned in a dam-strain of E. coli was digested with BglII and ClaI. A 238 bp fragment containing the tPA signal sequence was isolated. pCIStPA also was cut with ClaI and HpaI and a 5340 bp fragment isolated. This 5340 bp fragment contains the CMV enhancer, promoter, splice site, $Amp^R$ gene, E. coli origin, SV40 DHFR and the SV40 poly A site.

(3) pUC119 is digested with HindIII and XbaI to open the plasmid. The vector fragment is isolated and ligated to a HindIII-ClaI-XbaI adaptor oligonucleotide having the sequence as follows:

```
5' AGC TTG CGA TCG ATG CGT 3'
3'     ACG CTA GCT ACG CAG ATC 5'
``` the adaptor linked pUC119 plasmid (pUC119ClaId) is then digested with ClaI and XbaI to open the plasmid and the vector fragment isolated.

(4) A three part ligation is then performed creating ptPAEnksol by ligating (a) the 238 bp fragment (ClaI-BglII) from pCIStPA, (b) the 528 bp fragment (BamHI-XbaI) from pUC-5' Enksol, and (c) ClaI-XbaI digested pUC119ClaId vector fragment from step (3). This plasmid, ptPAEnksol is sequenced.

(5) The full length human cDNA is cut with SpeI, the resulting 5' overhang is blunted using Klenow, and the cDNA then digested with XbaI. A 2005 bp fragment containing the 3' end of the enkephalinase cDNA was recovered. ptPAEnksol from step (4) is digested with ClaI and XbaI and a 766 bp fragment is recovered encoding the tPA signal fused to the amino terminal domain of C-T deleted enkephalinase. A 3 part ligation is performed with the 5340 bp vector fragment of pCIStPA and the 766 bp fragment from step (5). The recombinant plasmid pCIS-Enksol is isolated from a transformant colony and its sequence confirmed.

Cytoplasmic Domain-Deleted Enkephalinase

A 149mer is chemically synthesized having the following sequence:

```
5'-GA TCC TGG ACT CCA CTG GAG ATC AGC CTC TCG GTC CTT GTC CTG CTC CTC ACC ATC ATA GCT-
3'       G ACC TGA GGT GAC CTC TAG TCG GAG AGC CAG GAA CAG GAC GAG GAG TGG TAG TAT CGA-

GTG ACA ATG ATC CGA CTC TAT GCA ACC TAC GAT GAT GGT ATT TGC AAG TCA TCA GAC TGC ATA AAA-
CAC TGT TAC TAG CGT GAG ATA CGT TGG ATG CTA CTA CCA TAA ACG TTC AGT AGT CTG ACG TAT TTT-

TCA GCT GCT CGA CT      3'
AGT CGA CGA GCT GAC TAG-5'.
```

This 149mer is ligated into the foregoing construction in place of the 53 bp oligonucleotide, resulting in pCIS-Enkinsol. This expression vector encodes cytoplasmic domain-deleted enkephalinase.

Human embryonic kidney line 293 (Graham et al., Id.) or CHO cells were transfected with either of pCIS-Enksol or pCIS-Enkinsol, stable transformants selected and, if desired, amplified in conventional fashion by use of the DHFR marker donated from pCIStPA. Cytoplasmic domain-deleted enkephalinase is recovered from the transformant culture of pCIS-Enkinsol transformants. Cytoplasmic and transmembrane domain-deleted enkephalinase is recovered from the culture of pCIS-Enksol transformants.

Full Length Human Enkephalinase

Figure 8:
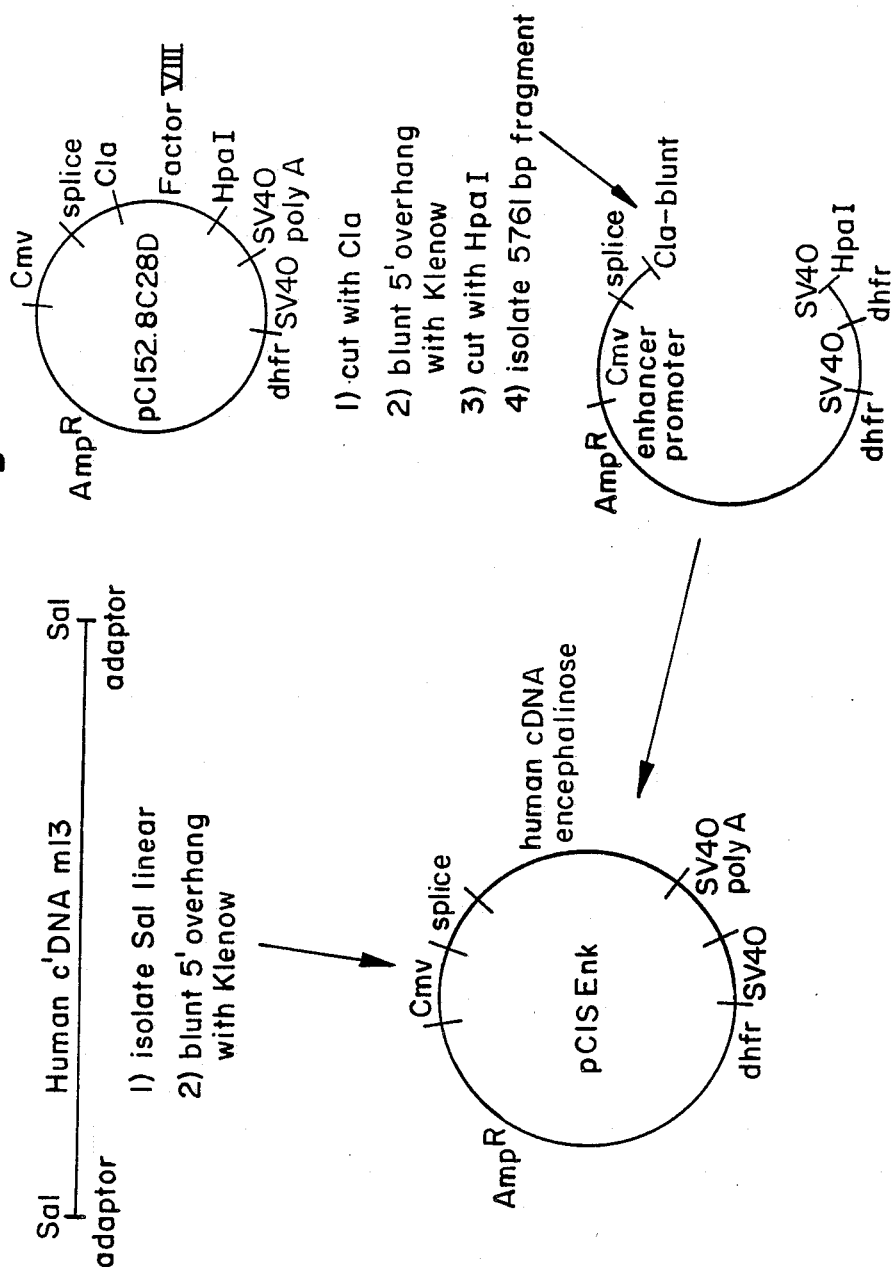
FIG. 8 A procedure for construction of an expression vector for full length human enkephalinase.

The full length human cDNA SalI fragment (including adaptor) is blunted using T4 DNA polymerase and ligated to pCIS2.8C28D which has been cleaved with HpaI and ClaI and blunted (FIG. 8). The recombinant plasmid, pCIShENK, (which has one cDNA encoding full length enkephalinase in the expression vector described above) is expressed in human embryonic kidney (293) cells and purified as described.

It should be appreciated that other suitable expression vectors are readily constructed by selection of suitable restriction sites and, if required, use of linkers or adaptors when inconvenient restriction sites are present. Also, partial digestions are conducted where required, i.e. where the designated fragments cannot be obtained under complete digestion conditions. Plasmid constructs are cloned in appropriate *E. coli* strains as will be known to those skilled in the art.

EXAMPLE 5

Assay for Detection of Enkephalinase

Enkephalinase activity has been measured using many different substrates, including tritiated enkephalins or analogs (Malfroy, B. et al., Nature 276: 523–526 [1978], Schwartz, J. C. et al., Life Sci. 29: 1715–1740 [1981] and Llorens, C. et al., J. Neurochem. 39: 1081–1089 [1982]) and fluorescent substrates in two-step assays (Orlowski, M. and Wilk, S., Biochemistry 20, 4942–4950 [1981]), Florentin, C. et al., Anal. Biochem. 141: 62–69 [1984] recently designed a novel fluorescent substrate that allows continuous recording of enkephalinase activity. This assay is based on the occurrence of intramolecular quenching of dansyl fluorescence by a nitrophenyl group. The following method uses novel fluorescent enkephalinase substrates based on energy transfer that also allow continuous recording of the enzyme activity.

Synthesis of Substrates

The peptides were synthesized via solid phase methodology. Barany, G. and Merrifield, R. B. in The Peptides 2:1–284 (Gross, E. and Meienhofer, J., Eds., Academic Press, N.Y., 1980). The dansyl group was introduced with dansyl chloride before the cleavage of the peptide from the resin support. After removal of the peptides from the support, purification was accomplished via preparative HPLC. Peptides were characterized by amino acid analysis and MNR.

Fluorometric Determination of the Hydrolysis of Dansylated Peptides

Fluorescence measurements were made using a Perkin Elmer, model 650-10S spectrofluorometer, equipped with a temperature controlled cell-holder, maintained at 37° C. Two procedures were used. The first combined a 50 μl solution of dansylated peptide with 50 μl of purified rat kidney enkephalinase in 50 mM, pH 7.4 HEPES buffer, containing 0.1% Tween 20, yielding a substrate concentration from 1 μM to 1 mM. After 1 hour at 37° C., 500 μl of 0.1M EDTA were added to the tubes. The 600 μl mixture was transferred into a quartz cuvette, and fluorescence measured. For dansyl-Gly-Trp-Gly, the excitation wavelength was set at 280 nm and emission at 360 nm. For the two tyrosine containing peptides, the excitation wavelength was at 277 nm and emission at 315 nm. Both slits were set at 2 nm. Known amounts of Trp-Gly and Tyr-Gly, diluted in the same mixture (100 μl HEPES, Tween 20, 500 μl EDTA), were run in parallel as standards. The fluorescence in the incubation media could thus be related to the amounts of hydrolyzed substrates. The second procedure permitted continuous monitoring of the hydrolysis of the dansylated peptides. A 500 μl solution of substrate at appropriate concentration, in 50 mM, pH 7.4 HEPES buffer containing 0.1% Tween 20 was pipetted in a quartz cuvette, and allowed to equilibrate in the cell holder of the fluorimeter at 37° C. Ten μl of purified rat kidney enkephalinase was added and the increase in tryptophan or tyrosine fluorescence was continuously monitored (excitation=280 nm, emission=360 nm for tryptophan, excitation 277, emission 315 for tyrosine). To minimize oxidation of tryptophan the intensity of excitation was reduced by adjusting the fluorimeter shutter so that a $10^{-4}$M solution of tryptophan in water gave a fluorescence of 20.0 with excitation set at 280 nm, emission at 360 nm, both slits at 2 nm, and sensitivity at 0.1. Under these conditions, tryptophan fluorescence was stable for over 2 hr.

Figure 5:
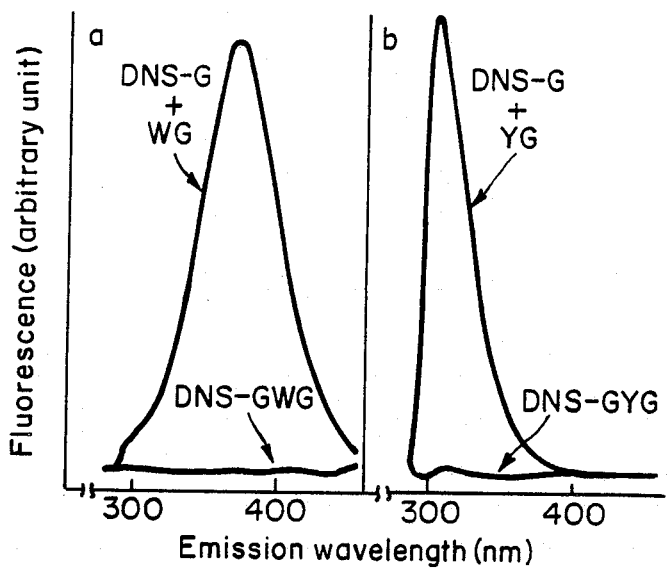
FIG. 5 Characterization of the fluorescence transfer between tryptophan and dansyl in dansyl-Gly-Trp-Gly and tyrosine and dansyl in dansyl-Gly-Tyr-Gly. Fluorescence spectra were obtained using $10^{-4}$M peptides in water at 37° C. Excitation was set at 280 nm. Slits were 2 nm for both excitation and emission. The sensitivity of the fluorimeter was ten times higher for the tyrosine containing peptides than for tryptophan.

When incubated with purified rat kidney enkephalinase, the peptides Gly-Trp-Gly, N-acetyl-Gly-Trp-Gly and dansyl-Gly-Trp-Gly were all hydrolysed at the Gly-Trp amide bond (FIG. 5). The unmodified tripeptide Gly-Trp-Gly was hydrolysed at a much lower rate than the two N-terminally substituted tripeptides. HPLC analysis demonstrated that the two peptides dansyl-Gly-Tyr-Gly and dansyl-Gly-Tyr-Gly-NH2 were hydrolysed at the Gly-Tyr amide bond. The hydrolysis of all substrates was completely inhibited when thiorphan was added in the reaction media.

Figure 6:
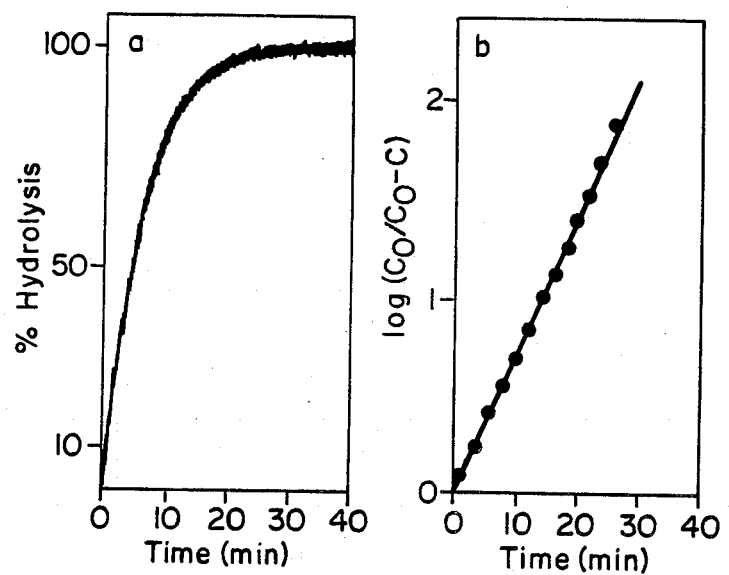
FIG. 6 Continuous fluorescence recording of the hydrolysis of dansyl-Gly-Trp-Gly by purified rat kidney enkephalinase. Purified rat kidney enkephalinase (350 ng) was added to 500 μl of dansyl-Gly-Trp-Gly ($5 \times 10^{-6}$M) in 50 mM HEPES buffer, pH 7.4, containing 0.1% Tween 20. Fluorescence (excitation 280 nm, emission 350 nm, slits set at 2 nm) was continuously recorded at 37° C. (a). The first order plot of substrate degradation (b) was obtained using measurements every 2 min, on the graph shown.

The fluorescence spectrum of dansyl-Gly-Trp-Gly was dramatically modified when the Gly-Trp amide bond was hydrolysed. Upon excitation at 280 nm the emission spectrum of dansyl-Gly-Trp-Gly showed a maximum at 540 nm, with no fluorescence detectable at 350 nm. In contrast, under the same conditions, the emission spectrum of the peptides dansyl-Gly and Trp-Gly in equimolar concentration showed a maximum at 350 nm, and a complete disappearance of fluorescence at 540 nm. In a similar way, upon excitation at 277 nm, the emission spectrum of peptides dansyl-Gly-Tyr-Gly and dansyl-Gly-Tyr-Gly-NH2 showed a maximum at 540 nm, while the maximum was at 315 nm for a mixture of the peptides dansyl-Gly and Tyr-Gly or, dansyl-Gly and Tyr-Gly-NH2 (FIG. 6b). This change in emission spectrum is indicative of a fluorescence transfer between the tryptophan residue and the dansyl group in the peptide dansyl-Gly-Trp-Gly, or between the tyrosine residue and the dansyl group in the peptides dansyl-Gly-Tyr-Gly and dansyl-Gly-Tyr-Gly-NH2.

When dansyl-Gly-Trp-Gly was incubated with purified rat kidney enkephalinase and under excitation at 280 nm, the hydrolysis of the Gly-Trp amide bond of the substrate induced an increase in fluorescence intensity at 350 nm, which could be continuously recorded. Similarly, the hydrolysis of peptides dansyl-Gly-Tyr-Gly and dansyl-Gly-Tyr-Gly-NH2 could be continuously recorded by following the increase in fluorescence intensity at 315 nm under excitation at 277 nm.

The kinetic parameters for the hydrolysis of dansyl-Gly-Trp-Gly, dansyl-Gly-Tyr-Gly and Dansyl-Tyr-Gly-NH2 by purified rat kidney enkephalinase were measured by incubating increasing concentrations of the substrates with the enzyme and stopping the reaction by the addition of EDTA before fluorescence measurements were taken (Table 4). Because tryptophan fluorescence increases with pH, the use of EDTA to stop the reactions resulted in an enhanced sensitivity in the assay when dansyl-Gly-Trp-Gly was used as the substrate.

TABLE 4

Kinetic parameters for the hydrolysis of various substrates by purified rat kidney enkephalinase

| | Substrate $P_2 P_1 P'_1 P'_2$ | $K_m(\mu M)$ | kcat (min$^{-1}$) | kcat/$K_m$ ($\mu M^{-1}$ min$^{-1}$) |
|---|---|---|---|---|
| I | Gly—Trp—Gly | | 53 | |
| II | N-acetyl-Gly—Trp—Gly | | 218 | |
| III | dansyl—Gly—Trp—Gly | 30 | 902 | 30 |
| IV | dansyl—Gly—Tyr—Gly | 41 | 1143 | 28 |
| V | dansyl—Gly—Tyr—Gly—NH2 | 90 | 248 | 3 |

$K_m$ and kcat values for substrates III, IV and V were obtained by measuring the increase in tryptophan or tyrosine fluorescence after 1 hr. incubations of increasing concentrations of substrates (from 1 $\mu$M to 1 mM) with 1 ng purified enzyme at 37° C. The kcat values for these substrates and peptides I and II were also obtained by HPLC analysis of 1 hr. incubations of 1 mM peptides with 200 ng (substrate I), 50 ng (substrates II and V), or 10 ng (substrates III and IV) enzyme. The kcat values obtained by both methods for substrates III, IV and V were in close agreement.

The specificity constant (kcat/$K_m$) of dansyl-Gly-Tyr-Gly-NH2 was much lower than that of the corresponding free carboxylic acid substrate dansyl-Gly-Tyr-Gly. This decrease in specificity constant was due both to an increased Km value and a decrease in kcat (Table 4).

EXAMPLE 6

Chemotactic Assay

The normal functions of mature neutrophils are chemotaxis, phagocytosis, microbicidal action, and digestion of foreign material. Chemotactic factors are generated at the site of inflammation which attract various immunological cells including neutrophils to that site. The mechanism underlying the chemotactic attraction of neutrophils to the inflammatory site is not fully understood. Enkephalinase has been implicated in the mechanism. Connelly, J. C. et al., Proc. Natl. Acad. Sci. (U.S.A.) 82, 8737–8741 (1985). In certain cases of hyperimmune responses abnormal influx of neutrophils and other immune cells may cause additional tissue damage.

Enkephalinase has been found to be bound to the cell membrane of human neutrophils. Connelly, et al., supra. Membrane bound enkephalinase from neutrophils cleaves the chemotactic peptide fMet-Leu-Phe. (Id.) Neutrophil degranulation and chemotaxis require cleavage of chemotactic peptides (Smith, R. et al., Fed. Proc. Fed. Am. Soc. Exp. Biol. 44, 576 [1985]) and Aswanikumar, S. et al., Proc. Natl. Acad. Sci. (U.S.A.) 73, 2439–2442 [1976]). Thus, it has been suggested that neutrophil membrane bound enkephalinase may be associated with the chemotactic signal by cleaving fMet-Leu-Phe in the immediate vicinity of the neutrophil receptor. This degradation would control the local concentration of the chemotactic peptide.

An assay was used to test the effects of enkephalinase on neutrophil chemotaxis. See U.S. patent application Ser. No. 06/707,005. Neutrophils were isolated by sedimentation over dextran from peripheral blood of human donors. A sample of neutrophils is placed over a 5 $\mu$m filter in a chemotaxis chamber containing aliquots of test material. Three to six replicates were run for each test for 1 hr. at 37° C. The number of migrating neutrophils in each chamber is then counted. The chemotactic potential is evaluated by the number of cells in five selected unit areas. A commercially available chemotaxis kit, Neuroprobe, Cabin John, Md. was used. Various specific inhibitors of enkephalinase were used to determine the role of enkephalinase in chemotaxis of neutrophils. Chemotactic activity is reported as the total number of neutrophils observed in five fields of the kit membrane under 100× magnification. Thus, the larger the number the more chemotactic was a particular test composition.

TABLE 5

Chemotactic Activity

| | Neutrophil Migration (% control) |
|---|---|
| Formyl Met—Leu—Phe 1 $\mu$M | 100 |
| Formyl Met—Leu—Phe + Thiorphan 10 $\mu$M | 29 ± 19 (n = 5) |
| Formyl Met—Leu—Phe + Phosphoramidon 10 $\mu$M | 65 (n = 1) |

Thus, neutrophil enkephalinase modulates chemotactic activity.

Pharmaceutical Compositions

The compounds of the present invention can be formulated according to known methods to prepare pharmaceutically useful compositions, whereby the enkephalinase product hereof is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host.

The enkephalinase hereof is administered for example to subjects suffering from kinin-mediated diseases or disorders in order to neutralize excessive bradykinin. In hypovolemic sequelae of hyperimmune reactions sterile enkephalinase is administered intravenously at dosages sufficient to resolve the hypovolemia as is readily determined by the clinician.

We claim:

1. A recombinant DNA selected from the group consisting of:
    (a) a rat DNA sequence encoding enkephalinase,
    (b) a human DNA sequence encoding enkephalinase, and
    (c) a DNA sequence which hybridizes to (a) or (b) and which encodes a mammalian enkephalinase.

2. The recombinant DNA of claim 1 wherein the recombinant DNA is a cDNA free of enkephalinase introns.

3. The recombinant DNA of claim 1 wherein the recombinant DNA is genomic DNA free of genomic DNA which encodes another polypeptide.

4. The recombinant DNA of claim 1 wherein DNA encoding the amino terminal transmembrane domain is deleted.

5. The recombinant DNA of claim 1 wherein DNA encoding the amino terminal cytoplasmic domain is deleted.

6. A recombinant DNA sequence coding for human enkephalinase wherein said DNA is substantially free of other human DNA sequences.

7. The recombinant DNA of claim 6 operatively linked to a promoter or control sequence.

8. The recombinant DNA of claim 1, wherein said DNA codes for a polypeptide having an amino acid sequence shown in FIG. 1.

9. The recombinant DNA of claim 1 that encodes human enkephalinase.

10. The recombinant DNA of claim 4 further comprising DNA encoding a cleavable signal sequence.

11. The recombinant DNA of claim 5 further comprising DNA encoding a cleavable signal sequence.

12. A recombinant expression vector comprising DNA encoding a mammalian enkephalinase of claim 1.

13. A cell transformed with the recombinant expression vector of claim 12.

14. The cell of claim 6 wherein the cell is a mammalian cell.

15. A process for producing a mammalian enkephalinase which comprises constructing a vector which includes DNA encoding a mammalian enkephalinase, of claim 1 transforming a host cell with the vector and culturing the transformed cell.

16. The process according to claim 15 which additionally comprises the step of recovering said enkephalinase.

17. The process according to claim 16 wherein the host cell is a eukaryotic cell.

18. The process of claim 17 wherein the eukaryotic cell is a chinese hamster ovary cell line.

19. The process of claim 17 wherein the eukaryotic cell is a human embryonic kidney cell line.

* * * * *